US012655399B2

(12) United States Patent
Zheng et al.

(10) Patent No.: US 12,655,399 B2
(45) Date of Patent: Jun. 16, 2026

(54) STABLE phi29 DNA POLYMERASE HAVING HIGH ENZYME ACTIVITY, AND ENCODING GENE AND APPLICATION THEREOF

(71) Applicant: BGI SHENZHEN, Shenzhen (CN)

(72) Inventors: Yue Zheng, Shenzhen (CN); Xun Xu, Shenzhen (CN); Wenwei Zhang, Shenzhen (CN); Yuliang Dong, Shenzhen (CN); Yujun Zhou, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 690 days.

(21) Appl. No.: 18/008,591

(22) PCT Filed: Oct. 10, 2020

(86) PCT No.: PCT/CN2020/120099
§ 371 (c)(1),
(2) Date: Dec. 6, 2022

(87) PCT Pub. No.: WO2021/248757
PCT Pub. Date: Dec. 16, 2021

(65) Prior Publication Data
US 2025/0270524 A1    Aug. 28, 2025

(30) Foreign Application Priority Data
Jun. 10, 2020    (CN) .......................... 202010523223.1

(51) Int. Cl.
*C12N 9/12*       (2006.01)
*C12N 15/70*      (2006.01)
*C12P 19/34*      (2006.01)

(52) U.S. Cl.
CPC ........... *C12N 9/1252* (2013.01); *C12N 15/70* (2013.01); *C12P 19/34* (2013.01); *C07K 2319/21* (2013.01); *C12Y 207/07007* (2013.01)

(58) Field of Classification Search
None
See application file for complete search history.

(56) References Cited

U.S. PATENT DOCUMENTS 9,422,535 B2 * 8/2016 Skirgaila ................. C12P 19/34
2014/0322759 A1 10/2014 Skirgaila et al.
2017/0015980 A1 1/2017 Skirgaila et al.

FOREIGN PATENT DOCUMENTS

| CN | 110573616 A | 12/2019 |
| CN | 110719955 A | 1/2020 |
| CN | 111172129 A | 5/2020 |
| EP | 2813576 A2 | 12/2014 |
| EP | 3617308 A1 | 3/2020 |
| WO | 2007076057 A2 | 7/2007 |
| WO | 2018195850 A1 | 11/2018 |
| WO | 2019019222 A1 | 1/2019 |
| WO | 2020073266 A1 | 4/2020 |

OTHER PUBLICATIONS

Singh et al. (Curr. Protein Pept. Sci. 18:1-11, 2017).*
Zhang et al. (Structure 26:1474-1485, 2018).*
Office Action issued for CN patent application serial No. 202080101598.7, dated Jul. 26, 2024, with English translation.
Search Report issued for EP patent application 20939885.8, dated Jul. 22, 2024.
"DNA polymerase Bacillus virusphi29" (2008).
Pérez-Arnaiz, P. et al. "φ29 DNA Polymerase Active Site: Role of Residue Val250 as Metal-dNTP Complex Ligand and in Protein-Primed Initiation" J. Mol. Biol. (2010) 395, 223-233.
English Translation of the Written Opinion of the International Search Authority, dated Mar. 2, 2021.
Search Report issued for EP patent application 20939885.8, dated Oct. 14, 2024.
Prado, A.D. et al. "The Loop of the TPR1 Subdomain of Phi29 DNA Polymerase Plays a Pivotal Role in Primer-Terminus Stabilization at the Polymerization Active Site" Biomolecules, vol. 9, Oct. 24, 2019, article No. 648.
Vega, M. et al. "Primer-terminus stabilization at the 3'-5' exonuclease active site of phi29 DNA polymerase. Involvement of two amino acid residues highly conserved in proofreading DNA polymerases" EMBO J., vol. 15, No. 5, Dec. 31, 1996, pp. 1182-1192.
International Search Report issued for PCT/CN2020/120099, dated Mar. 2, 2021.
Written Opinion of the International Searching Authority issued for PCT/CN2020/120099, dated Mar. 2, 2021.

* cited by examiner

*Primary Examiner* — Richard G Hutson
(74) *Attorney, Agent, or Firm* — Westman, Champlin & Koehler, P.A.; Z. Peter Sawicki

(57)    ABSTRACT

Provided are a stable Phi29 DNA polymerase having high enzyme activity, and an encoding gene and an application thereof. The Phi29 DNA polymerase is obtained by substituting amino acid residue at at least one among the following 29 positions: position 17, position 96, position 97, position 99, position 123, position 140, position 148, position 158, position 159, position 171, position 203, position 204, position 213, position 217, position 224, position 250, position 270, position 309, position 310, position 320, position 344, position 345, position 347, position 369, position 402, position 416, position 509, position 515 and position 524 of a DNA polymerase shown in SEQ ID NO: 2.

6 Claims, 1 Drawing Sheet

Specification includes a Sequence Listing.

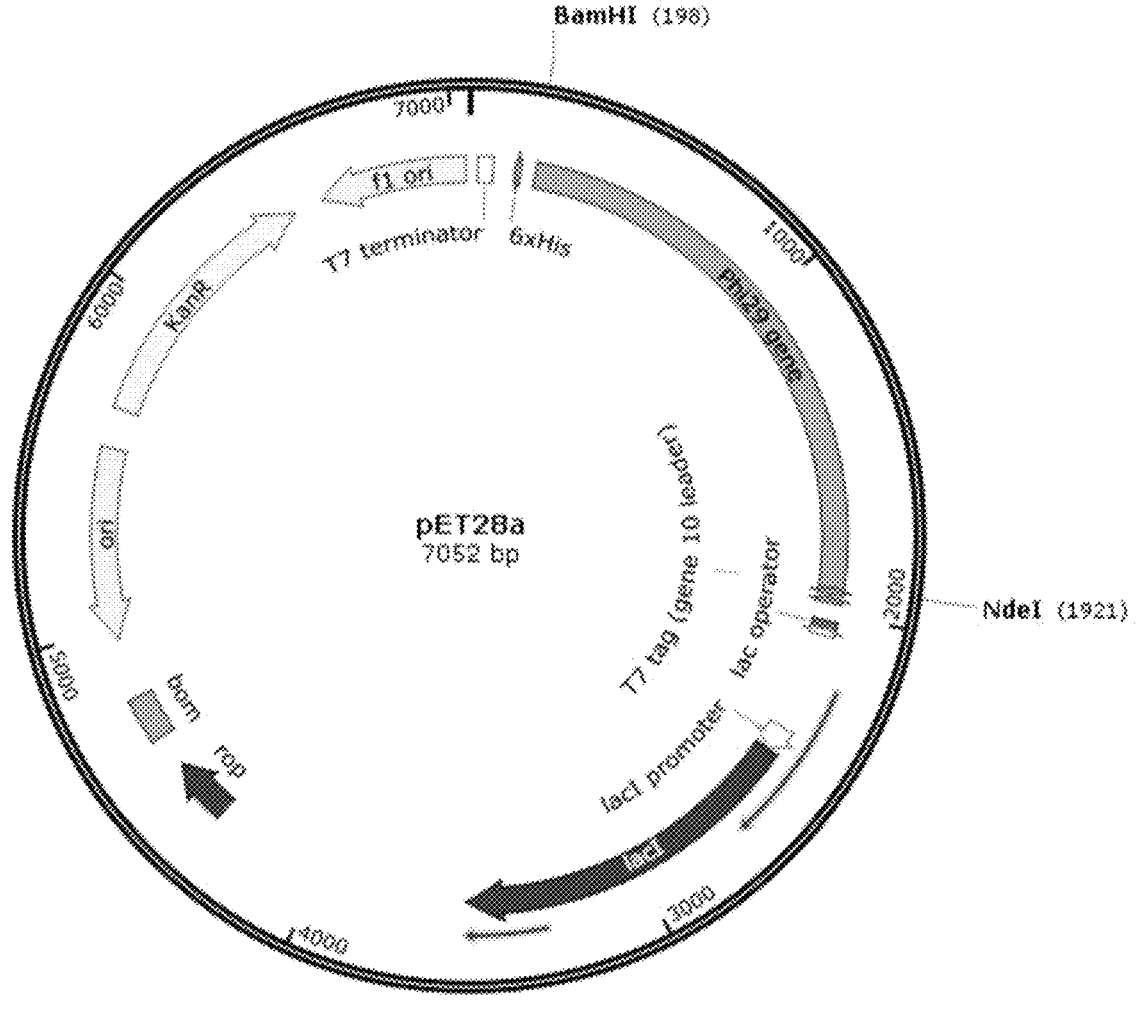

STABLE phi29 DNA POLYMERASE HAVING HIGH ENZYME ACTIVITY, AND ENCODING GENE AND APPLICATION THEREOF

CROSS-REFERENCE TO RELATED APPLICATION

This Application is a Section 371 National Stage Application of International Application No. PCT/CN2020/120099, filed Oct. 10, 2020 and published as WO2021/248757 on Dec. 16, 2021, in Chinese, which claims priority to CN patent application No. 202010523223.1, filed Jun. 10, 2020 the contents of which are hereby incorporated by reference in their entirety.

FIELD

The present disclosure relates to the field of biological technology, and specifically relates to a stable phi29 DNA polymerase having high enzyme activity, and an encoding gene and application thereof.

BACKGROUND

Phi29 DNA polymerase, a thermophilic DNA polymerase cloned from *Bacillus subtilis* phage Phi29, is obtained by purification and isolation for multiple times after expressed in the *Escherichia coli* (*E. coli*) via gene recombination technology. The phi29 DNA polymerase is widely used in different isothermal amplification due to its specific strand displacement activity, high fidelity and processivity, such as rolling cycle amplification (RCA), multiple displacement amplification (MDA), loop-mediated isothermal amplification (LAMP) and so on. On the DNB-SEQ series of sequencing platforms, the phi29 DNA polymerase is mainly used in applications of DNB making and a second strand amplification. However, poor stability of wide-type Phi29 DNA polymerase and commercial phi29 DNA polymerase cannot meet requirements for presenting as a kit, for example, the wide-type Phi29 DNA polymerase is stable for less than one year and has a low reaction rate, thus exhibiting a poor sequencing quality when used for DNB-SEQ. Accordingly, it is of great significance to improve the stability and/or enzyme activity of the phi29 DNA polymerase.

SUMMARY

The present disclosure aims at providing a phi29 DNA polymerase with an improved stability and/or enzyme activity (e.g., specific enzyme activity).

In a first aspect, the present disclosure provides in embodiments a protein which may be C1) or C2), wherein C1) is a protein having DNA polymerase activity obtained by substituting an amino acid residue at at least one of the following 29 positions of a phi29 DNA polymerase: position 17, position 96, position 97, position 99, position 123, position 140, position 148, position 158, position 159, position 171, position 203, position 204, position 213, position 217, position 224, position 250, position 270, position 309, position 310, position 320, position 344, position 345, position 347, position 369, position 402, position 416, position 509, position 515 and position 524;

C2) is a fusion protein obtained by attaching a tag to the N-terminus or/and C-terminus of the protein of C1), wherein an amino acid sequence of the phi29 DNA polymerase is set forth in SEQ ID NO: 2.

In the above proteins, T at position 17 may be substituted with P; R at position 96 may be substituted with E, N, S, A, G or K; M at position 97 may be substituted with Y, S, R, Q, G, C, P, V, W, N, D, E or T; Q at position 99 may be substituted with V, E or T; L at position 123 may be substituted with Y, A, C, Q, M, N or P; T at position 140 may be substituted with K or H; Y at position 148 may be substituted with P or E; I at position 158 may be substituted with P; T at position 159 may be substituted with A; Q at position 171 may be substituted with E or K; T at position 203 may be substituted with E; T at position 204 may be substituted with K; T at position 213 may be substituted with K; G at position 217 may be substituted with K; Y at position 224 may be substituted with E or K; V at position 250 may be substituted with I; V at position 270 may be substituted with R; F at position 309 may be substituted with S; Y at position 310 may be substituted with N or G; G at position 320 may be substituted with H, E, D or C; N at position 344 may be substituted with R or K; V at position 345 may be substituted with E; Y at position 347 may be substituted with G; Y at position 369 may be substituted with D or N; K at position 402 may be substituted with L; L at position 416 may be substituted with A; V at position 509 may be substituted with E; E at position 515 may be substituted with W, T, S, R, N, I, F, H, Q or T; I at position 524 may be substituted with V.

Any one of the proteins as described above exhibits higher stability and/or specific enzyme activity than that of the phi29 DNA polymerase.

Specifically, any one of the proteins as described above may be a recombinant phi29 DNA polymerase with T213K/L416A/V509E mutations, a recombinant phi29 DNA polymerase with M97T/Y224K/E515S mutations or a recombinant phi29 DNA polymerase with R96S/L123P/Y224K/L416A/E515S mutations.

The recombinant phi29 DNA polymerase with T213K/L416A/V509E mutations may be a protein obtained by substituting T at position 213 with K, L at position 416 with A and V at position 509 with E, from the N-terminus of SEQ ID NO: 2.

The recombinant phi29 DNA polymerase with M97T/Y224K/E515S mutations may be a protein obtained by substituting M at position 97 with T, Y at position 224 with K and E at position 515 with S, from the N-terminus of SEQ ID NO: 2.

The recombinant phi29 DNA polymerase with R96S/L123P/Y224K/L416A/E515S mutations may be a protein obtained by substituting R at position 96 with S, L at position 123 with P, Y at position 224 with K, L at position 416 with A and E at position 515 with S, from the N-terminus of SEQ ID NO: 2.

Any one of the proteins as described above may be any one of proteins a1 to a70.

Protein a1 is a protein obtained by substituting T at position 17 with P from the N-terminus of SEQ ID NO: 2; protein a2 is a protein obtained by substituting M at position 97 with Y from the N-terminus of SEQ ID NO: 2; protein a3 is a protein obtained by substituting M at position 97 with S from the N-terminus of SEQ ID NO: 2; protein a4 is a protein obtained by substituting M at position 97 with R from the N-terminus of SEQ ID NO: 2; protein a5 is a protein obtained by substituting M at position 97 with Q from the N-terminus of SEQ ID NO: 2; protein a6 is a protein obtained by substituting M at position 97 with G from the N-terminus of SEQ ID NO: 2; protein a7 is a protein obtained by substituting L at position 123 with Y from the N-terminus of SEQ ID NO: 2; protein a8 is a protein obtained by substituting T at position 140 with K from the N-terminus of SEQ ID NO: 2; protein a9 is a protein obtained by substituting T at position 140 with H from the N-terminus of SEQ ID NO: 2; protein a10 is a protein obtained by substituting Y at position 148 with P from the N-terminus of SEQ ID NO: 2; protein a11 is a protein obtained by substituting Y at position 148 with E from the N-terminus of SEQ ID NO: 2; protein a12 is a protein obtained by substituting I at position 158 with P from the N-terminus of SEQ ID NO: 2; protein a13 is a protein obtained by substituting T at position 159 with A from the N-terminus of SEQ ID NO: 2; protein a14 is a protein obtained by substituting T at position 203 with E from the N-terminus of SEQ ID NO: 2; protein a15 is a protein obtained by substituting Y at position 224 with E from the N-terminus of SEQ ID NO: 2; protein a16 is a protein obtained by substituting F at position 309 with S from the N-terminus of SEQ ID NO: 2; protein a17 is a protein obtained by substituting Y at position 310 with N from the N-terminus of SEQ ID NO: 2; protein a18 is a protein obtained by substituting Y at position 310 with G from the N-terminus of SEQ ID NO: 2; protein a19 is a protein obtained by substituting G at position 320 with H from the N-terminus of SEQ ID NO: 2; protein a20 is a protein obtained by substituting G at position 320 with E from the N-terminus of SEQ ID NO: 2; protein a21 is a protein obtained by substituting G at position 320 with D from the N-terminus of SEQ ID NO: 2; protein a22 is a protein obtained by substituting G at position 320 with C from the N-terminus of SEQ ID NO: 2; protein a23 is a protein obtained by substituting N at position 344 with R from the N-terminus of SEQ ID NO: 2; protein a24 is a protein obtained by substituting V at position 345 with E from the N-terminus of SEQ ID NO: 2; protein a25 is a protein obtained by substituting Y at position 347 with G from the N-terminus of SEQ ID NO: 2; protein a26 is a protein obtained by substituting V at position 509 with E from the N-terminus of SEQ ID NO: 2; protein a27 is a protein obtained by substituting E at position 515 with W from the N-terminus of SEQ ID NO: 2; protein a28 is a protein obtained by substituting E at position 515 with T from the N-terminus of SEQ ID NO: 2; protein a29 is a protein obtained by substituting E at position 515 with S from the N-terminus of SEQ ID NO: 2; protein a30 is a protein obtained by substituting E at position 515 with R from the N-terminus of SEQ ID NO: 2; protein a31 is a protein obtained by substituting E at position 515 with N from the N-terminus of SEQ ID NO: 2; protein a32 is a protein obtained by substituting E at position 515 with I from the N-terminus of SEQ ID NO: 2; protein a33 is a protein obtained by substituting E at position 515 with F from the N-terminus of SEQ ID NO: 2; protein a34 is a protein obtained by substituting R at position 96 with E from the N-terminus of SEQ ID NO: 2; protein a35 is a protein obtained by substituting R at position 96 with N from the N-terminus of SEQ ID NO: 2; protein a36 is a protein obtained by substituting R at position 96 with S from the N-terminus of SEQ ID NO: 2; protein a37 is a protein obtained by substituting R at position 96 with A from the N-terminus of SEQ ID NO: 2; protein a38 is a protein obtained by substituting R at position 96 with G from the N-terminus of SEQ ID NO: 2; protein a39 is a protein obtained by substituting R at position 96 with K from the N-terminus of SEQ ID NO: 2; protein a40 is a protein obtained by substituting M at position 97 with C from the N-terminus of SEQ ID NO: 2; protein a41 is a protein obtained by substituting M at position 97 with P from the N-terminus of SEQ ID NO: 2; protein a42 is a protein obtained by substituting M at position 97 with V from the N-terminus of SEQ ID NO: 2; protein a43 is a protein obtained by substituting M at position 97 with W from the N-terminus of SEQ ID NO: 2; protein a44 is a protein obtained by substituting M at position 97 with N from the N-terminus of SEQ ID NO: 2; protein a45 is a protein obtained by substituting M at position 97 with D from the N-terminus of SEQ ID NO: 2; protein a46 is a protein obtained by substituting M at position 97 with E from the N-terminus of SEQ ID NO: 2; protein a47 is a protein obtained by substituting Q at position 99 with V from the N-terminus of SEQ ID NO: 2; protein a48 is a protein obtained by substituting Q at position 99 with E from the N-terminus of SEQ ID NO: 2; protein a49 is a protein obtained by substituting Q at position 99 with T from the N-terminus of SEQ ID NO: 2; protein a50 is a protein obtained by substituting L at position 123 with A from the N-terminus of SEQ ID NO: 2; protein a51 is a protein obtained by substituting L at position 123 with C from the N-terminus of SEQ ID NO: 2; protein a52 is a protein obtained by substituting L at position 123 with Q from the N-terminus of SEQ ID NO: 2; protein a53 is a protein obtained by substituting L at position 123 with M from the N-terminus of SEQ ID NO: 2; protein a54 is a protein obtained by substituting L at position 123 with N from the N-terminus of SEQ ID NO: 2; protein a55 is a protein obtained by substituting Q at position 171 with E from the N-terminus of SEQ ID NO: 2; protein a56 is a protein obtained by substituting Q at position 171 with K from the N-terminus of SEQ ID NO: 2; protein a57 is a protein obtained by substituting T at position 204 with K from the N-terminus of SEQ ID NO: 2; protein a58 is a protein obtained by substituting T at position 213 with K from the N-terminus of SEQ ID NO: 2; protein a59 is a protein obtained by substituting G at position 217 with K from the N-terminus of SEQ ID NO: 2; protein a60 is a protein obtained by substituting V at position 250 with I from the N-terminus of SEQ ID NO: 2; protein a61 is a protein obtained by substituting V at position 270 with R from the N-terminus of SEQ ID NO: 2; protein a62 is a protein obtained by substituting N at position 344 with K from the N-terminus of SEQ ID NO: 2; protein a63 is a protein obtained by substituting Y at position 369 with D from the N-terminus of SEQ ID NO: 2; protein a64 is a protein obtained by substituting Y at position 369 with N from the N-terminus of SEQ ID NO: 2; protein a65 is a protein obtained by substituting K at position 402 with L from the N-terminus of SEQ ID NO: 2; protein a66 is a protein obtained by substituting L at position 416 with A from the N-terminus of SEQ ID NO: 2; protein a67 is a protein obtained by substituting E at position 515 with H from the N-terminus of SEQ ID NO: 2; protein a68 is a protein obtained by substituting E at position 515 with Q from the N-terminus of SEQ ID NO: 2; protein a69 is a protein obtained by substituting E at position 515 with T from the N-terminus of SEQ ID NO: 2; protein a70 is a protein obtained by substituting I at position 524 with V from the N-terminus of SEQ ID NO: 2.

Any one of the proteins as described above may be any one of proteins b1 to b70.

Protein b1 is a protein obtained by substituting T at position 37 with P from the N-terminus of SEQ ID NO: 4; protein b2 is a protein obtained by substituting M at position 117 with Y from the N-terminus of SEQ ID NO: 4; protein b3 is a protein obtained by substituting M at position 117 with S from the N-terminus of SEQ ID NO: 4; protein b4 is a protein obtained by substituting M at position 117 with R from the N-terminus of SEQ ID NO: 4; protein b5 is a protein obtained by substituting M at position 117 with Q from the N-terminus of SEQ ID NO: 4; protein b6 is a protein obtained by substituting M at position 117 with G from the N-terminus of SEQ ID NO: 4; protein b7 is a protein obtained by substituting L at position 143 with Y from the N-terminus of SEQ ID NO: 4; protein b8 is a protein obtained by substituting T at position 160 with K from the N-terminus of SEQ ID NO: 4; protein b9 is a protein obtained by substituting T at position 160 with H from the N-terminus of SEQ ID NO: 4; protein b10 is a protein obtained by substituting Y at position 168 with P from the N-terminus of SEQ ID NO: 4; protein b11 is a protein obtained by substituting Y at position 168 with E from the N-terminus of SEQ ID NO: 4; protein b12 is a protein obtained by substituting I at position 178 with P from the N-terminus of SEQ ID NO: 4; protein b13 is a protein obtained by substituting T at position 179 with A from the N-terminus of SEQ ID NO: 4; protein b14 is a protein obtained by substituting T at position 223 with E from the N-terminus of SEQ ID NO: 4; protein b15 is a protein obtained by substituting Y at position 244 with E from the N-terminus of SEQ ID NO: 4; protein b16 is a protein obtained by substituting F at position 329 with S from the N-terminus of SEQ ID NO: 4; protein b17 is a protein obtained by substituting Y at position 330 with N from the N-terminus of SEQ ID NO: 4; protein b18 is a protein obtained by substituting Y at position 330 with G from the N-terminus of SEQ ID NO: 4; protein b19 is a protein obtained by substituting G at position 340 with H from the N-terminus of SEQ ID NO: 4; protein b20 is a protein obtained by substituting G at position 340 with E from the N-terminus of SEQ ID NO: 4; protein b21 is a protein obtained by substituting G at position 340 with D from the N-terminus of SEQ ID NO: 4; protein b22 is a protein obtained by substituting G at position 340 with C from the N-terminus of SEQ ID NO: 4; protein b23 is a protein obtained by substituting N at position 364 with R from the N-terminus of SEQ ID NO: 4; protein b24 is a protein obtained by substituting V at position 365 with E from the N-terminus of SEQ ID NO: 4; protein b25 is a protein obtained by substituting Y at position 367 with G from the N-terminus of SEQ ID NO: 4; protein b26 is a protein obtained by substituting V at position 529 with E from the N-terminus of SEQ ID NO: 4; protein b27 is a protein obtained by substituting E at position 535 with W from the N-terminus of SEQ ID NO: 4; protein b28 is a protein obtained by substituting E at position 535 with T from the N-terminus of SEQ ID NO: 4; protein b29 is a protein obtained by substituting E at position 535 with S from the N-terminus of SEQ ID NO: 4; protein b30 is a protein obtained by substituting E at position 535 with R from the N-terminus of SEQ ID NO: 4; protein b31 is a protein obtained by substituting E at position 535 with N from the N-terminus of SEQ ID NO: 4; protein b32 is a protein obtained by substituting E at position 535 with I from the N-terminus of SEQ ID NO: 4; protein b33 is a protein obtained by substituting E at position 535 with F from the N-terminus of SEQ ID NO: 4; protein b34 is a protein obtained by substituting R at position 116 with E from the N-terminus of SEQ ID NO: 4; protein b35 is a protein obtained by substituting R at position 116 with N from the N-terminus of SEQ ID NO: 4; protein b36 is a protein obtained by substituting R at position 116 with S from the N-terminus of SEQ ID NO: 4; protein b37 is a protein obtained by substituting R at position 116 with A from the N-terminus of SEQ ID NO: 4; protein b38 is a protein obtained by substituting R at position 116 with G from the N-terminus of SEQ ID NO: 4; protein b39 is a protein obtained by substituting R at position 116 with K from the N-terminus of SEQ ID NO: 4; protein b40 is a protein obtained by substituting M at position 117 with C from the N-terminus of SEQ ID NO: 4; protein b41 is a protein obtained by substituting M at position 117 with P from the N-terminus of SEQ ID NO: 4; protein b42 is a protein obtained by substituting M at position 117 with V from the N-terminus of SEQ ID NO: 4; protein b43 is a protein obtained by substituting M at position 117 with W from the N-terminus of SEQ ID NO: 4; protein b44 is a protein obtained by substituting M at position 117 with N from the N-terminus of SEQ ID NO: 4; protein b45 is a protein obtained by substituting M at position 117 with D from the N-terminus of SEQ ID NO: 4; protein b46 is a protein obtained by substituting M at position 117 with E from the N-terminus of SEQ ID NO: 4; protein b47 is a protein obtained by substituting Q at position 119 with V from the N-terminus of SEQ ID NO: 4; protein b48 is a protein obtained by substituting Q at position 119 with E from the N-terminus of SEQ ID NO: 4; protein b49 is a protein obtained by substituting Q at position 119 with T from the N-terminus of SEQ ID NO: 4; protein b50 is a protein obtained by substituting L at position 143 with A from the N-terminus of SEQ ID NO: 4; protein b51 is a protein obtained by substituting L at position 143 with C from the N-terminus of SEQ ID NO: 4; protein b52 is a protein obtained by substituting L at position 143 with Q from the N-terminus of SEQ ID NO: 4; protein b53 is a protein obtained by substituting L at position 143 with M from the N-terminus of SEQ ID NO: 4; protein b54 is a protein obtained by substituting L at position 143 with N from the N-terminus of SEQ ID NO: 4; protein b55 is a protein obtained by substituting Q at position 191 with E from the N-terminus of SEQ ID NO: 4; protein b56 is a protein obtained by substituting Q at position 191 with K from the N-terminus of SEQ ID NO: 4; protein b57 is a protein obtained by substituting T at position 224 with K from the N-terminus of SEQ ID NO: 4; protein b58 is a protein obtained by substituting T at position 233 with K from the N-terminus of SEQ ID NO: 4; protein b59 is a protein obtained by substituting G at position 237 with K from the N-terminus of SEQ ID NO: 4; protein b60 is a protein obtained by substituting V at position 270 with I from the N-terminus of SEQ ID NO: 4; protein b61 is a protein obtained by substituting V at position 290 with R from the N-terminus of SEQ ID NO: 4; protein b62 is a protein obtained by substituting N at position 364 with K from the N-terminus of SEQ ID NO: 4; protein b63 is a protein obtained by substituting Y at position 389 with D from the N-terminus of SEQ ID NO: 4; protein b64 is a protein obtained by substituting Y at position 389 with N from the N-terminus of SEQ ID NO: 4; protein b65 is a protein obtained by substituting K at position 422 with L from the N-terminus of SEQ ID NO: 4; protein b66 is a protein obtained by substituting L at position 436 with A from the N-terminus of SEQ ID NO: 4; protein b67 is a protein obtained by substituting E at position 535 with H from the N-terminus of SEQ ID NO: 4; protein b68 is a protein obtained by substituting E at position 535 with Q from the N-terminus of SEQ ID NO: 4; protein b69 is a protein obtained by substituting E at position 535 with T from the N-terminus of SEQ ID NO: 4; protein b70 is a protein obtained by substituting I at position 544 with V from the N-terminus of SEQ ID NO: 4.

A nucleic acid molecule encoding a protein of any one of the proteins as described above is also drawn into the protect scope of the present disclosure.

An expression cassette, a recombinant vector, a recombinant microorganism or a transgenic cell line comprising the nucleic acid molecule is also drawn into the protect scope of the present disclosure.

The recombinant vector may be a recombinant plasmid obtained by inserting the nucleic acid molecule into an expression vector or a cloning vector. Specifically, the expression vector may be a pET28a (+) vector.

Specifically, the recombinant vector may be a recombinant pET28a-T17P vector, a recombinant pET28a-M97Y vector, a recombinant pET28a-M97S vector, a recombinant pET28a-M97R vector, a recombinant pET28a-M97Q vector, a recombinant pET28a-M97G vector, a recombinant pET28a-L123Y vector, a recombinant pET28a-T140K vector, a recombinant pET28a-T140H vector, a recombinant pET28a-Y148P vector, a recombinant pET28a-Y148E vector, a recombinant pET28a-1158P vector, a recombinant pET28a-T159A vector, a recombinant pET28a-T203E vector, a recombinant pET28a-Y224E vector, a recombinant pET28a-F309S vector, a recombinant pET28a-Y310N vector, a recombinant pET28a-Y310G vector, a recombinant pET28a-G320H vector, a recombinant pET28a-G320E vector, a recombinant pET28a-G320D vector, a recombinant pET28a-G320C vector, a recombinant pET28a-N344R vector, a recombinant pET28a-V345E vector, a recombinant pET28a-Y347G vector, a recombinant pET28a-V509E vector, a recombinant pET28a-E515W vector, a recombinant pET28a-E515T vector, a recombinant pET28a-E515S vector, a recombinant pET28a-E515R vector, a recombinant pET28a-E515N vector, a recombinant pET28a-E515I vector, a recombinant pET28a-E515F vector, a recombinant pET28a-R96E vector, a recombinant pET28a-R96N vector, a recombinant pET28a-R96S vector, a recombinant pET28a-R96A vector, a recombinant pET28a-R96G vector, a recombinant pET28a-R96K vector, a recombinant pET28a-M97C vector, a recombinant pET28a-M97P vector, a recombinant pET28a-M97V vector, a recombinant pET28a-M97W vector, a recombinant pET28a-M97N vector, a recombinant pET28a-M97D vector, a recombinant pET28a-M97E vector, a recombinant pET28a-Q99V vector, a recombinant pET28a-Q99E vector, a recombinant pET28a-Q99T vector, a recombinant pET28a-L123A vector, a recombinant pET28a-L123C vector, a recombinant pET28a-L123Q vector, a recombinant pET28a-L123M vector, a recombinant pET28a-L123N vector, a recombinant pET28a-Q171E vector, a recombinant pET28a-Q171K vector, a recombinant pET28a-T204K vector, a recombinant pET28a-T213K vector, a recombinant pET28a-G217K vector, a recombinant pET28a-V250I vector, a recombinant pET28a-V270R vector, a recombinant pET28a-N344K vector, a recombinant pET28a-Y369D vector, a recombinant pET28a-Y369N vector, a recombinant pET28a-K402L vector, a recombinant pET28a-L416A vector, a recombinant pET28a-E515H vector, a recombinant pET28a-E515Q vector, a recombinant pET28a-E515T or a recombinant pET28a-1524V, mentioned in embodiments of the present disclosure.

The recombinant microorganism is a recombinant bacterium obtained by introducing the recombinant vector into an initial microorganism.

The initial microorganism may be *E. coli*.

Specifically, the *E. coli* may be *E. coli* BL21 (DE3).

Use of any one of the proteins or the nucleic acid molecules as described above in preparation of a DNA polymerase is also drawn into the protect scope of the present disclosure.

In the above use, the recombinant DNA polymerase exhibits higher stability and/or specific enzyme activity than that of a phi29 DNA polymerase.

Use of any one of the proteins or the nucleic acid molecules as described above in PCR amplification or sequencing is also drawn into the protect scope of the present disclosure.

In the above use, the PCR amplification may be second strand amplification, single cell amplification and/or plasmid amplification; and the sequencing may be DNB SEQ sequencing.

Use of any one of the proteins or the nucleic acid molecules as described above in preparation of a product for sequencing is also drawn into the protect scope of the present disclosure.

In the above use, the product may be a kit.

The inventors of the present disclosure have conducted site-directed mutagenesis on the existing phi29 DNA polymerase through a large number of experiments, and further used DNA shuffling and a combined-mutation construction method to construct a combined mutant, and prepared 73 recombinant phi29 DNA polymerases with significantly improved stability and/or specific enzyme activity. These recombinant phi29 DNA polymerases not only have improved thermal stability, but also exhibit increased polymerization activity and processivity. When the recombinant phi29 DNA polymerases prepared in the present disclosure are used in amplification or sequencing, DNA can be efficiently and continuously synthesized, and the reaction efficiency is high. The present disclosure has important application value.

BRIEF DESCRIPTION OF THE DRAWINGS

FIG. 1 is a structure diagram showing a pET28a (+) vector.

DETAILED DESCRIPTION OF THE DISCLOSURE

The following examples are for better understanding of the present disclosure rather than limiting.

Unless otherwise specified, the experimental methods in the following examples are conventional methods.

The test materials used in the following examples are purchased from conventional biochemical reagent companies, unless otherwise specified.

The quantitative experiments in the following examples are all set up in triplicate, with averaged results.

The pET28a (+) vector is purchased from Novagen Company, a structure diagram of which is shown in FIG. 1.

Affinity solution A was an aqueous solution containing 20 mM of Tris-HCl, 500 mM of NaCl, 20 mM of Imidazole and 62.5 g/L of Glycerol, pH value of which was 7.9.

Recombinant phi29 DNA polymerases in Examples 1, 2 and 3 were phi29 DNA polymerases with a single mutation, while recombinant phi29 DNA polymerases in Examples 4 were phi29 DNA polymerases with combined mutations.

Example 1: Preparation of a Crude Recombinant Phi29 DNA Polymerase 1.1 Construction of a Recombinant Plasmid pET28a-WT A short DNA fragment between the sequences recognized by restriction enzymes of NdeI and BamHI in pET28a (+) was replaced by a double-stranded DNA molecule as shown in SEQ ID NO: 1, and other sequences were unchanged, thereby obtaining the recombinant plasmid pET28a-WT.

The double-stranded DNA molecule as shown in SEQ ID NO: 1 was a coding gene for the Phi29 DNA polymerase, which encodes the Phi29 DNA polymerase with an amino acid sequence as shown in SEQ ID NO: 2.

The recombinant plasmid pET28a-WT was sequenced. The sequencing results showed that in the recombinant plasmid pET28a-WT, the double-stranded DNA molecule shown in SEQ ID NO: 1 was fused with a coding sequence of a His-tag composed of 6 histidine residues on the vector backbone, forming a fusion gene as shown in SEQ ID NO: 3 that expressed the recombinant Phi29 DNA polymerase as shown in SEQ ID NO: 4, which was named as fusion protein 1, where the fusion protein 1 with the His-tag.

1.2 Site-Directed Mutagenesis of the Coding Gene of the Phi29 DNA Polymerase 1.2.1 A PCR reaction system for the site-directed mutagenesis was prepared. The PCR reaction system for the site-directed mutagenesis was in a volume of 25 µl, including 2.5 µl of 10×Pfu Reaction Buffer with $Mg^{2+}$; 2 µl of dNTP Mix, where the concentrations of dATP, dTTP, dGTP and dCTP each were 2.5 mM; 25 ng of the recombinant plasmid pET28a-WT; 0.5 µl of Pfu DNA Polymerase; and a primer for introducing a mutation.

Pfu DNA Polymerase is purchased from ThermoFisher Company with Cat. No. EP0501. 10×Pfu Reaction Buffer with $Mg^{2+}$ is a component of Pfu DNA Polymerase.

The primers for introducing a mutation are shown in Table 1.

TABLE 1

| mutation site | nucleotide sequence of forward primer (5'-3') | nucleotide sequence of reverse primer (5'-3') |
| --- | --- | --- |
| T17P | GACTTTGAAACCACCCCGAAAGT GGAAGATTGC (SEQ ID NO: 5) | GCAATCTTCCACTTTCGGGGTGGT TTCAAAGTC (SEQ ID NO: 6) |
| M97Y | GATATCAATCATATACCACTGGC CATAGCGGCTAATAATGGTGTTA TAGGT (SEQ ID NO: 7) | ACCTATAACACCATTATTAGCCGC TATGGCCAGTGGTATATGATTGAT ATC (SEQ ID NO: 8) |
| M97S | CATATACCACTGGCCGCTGCGGC TAATAATGGTGTTATAGG (SEQ ID NO: 9) | CCTATAACACCATTATTAGCCGCA GCGGCCAGTGGTATATG (SEQ ID NO: 10) |
| M97R | TACCACTGGCCCCTGCGGCTAAT AATGGTGTTATAG (SEQ ID NO: 11) | CTATAACACCATTATTAGCCGCAG GGGCCAGTGGTA (SEQ ID NO: 12) |
| M97Q | CAATCATATACCACTGGCCCTGG CGGCTAATAATGGTGTTAT (SEQ ID NO: 13) | ATAACACCATTATTAGCCGCCAGG GCCAGTGGTATATGATTG (SEQ ID NO: 14) |
| M97G | CAATCATATACCACTGGCCCCCG CGGCTAATAATGGTGTTAT (SEQ ID NO: 15) | ATAACACCATTATTAGCCGCGGGG GCCAGTGGTATATGATTG (SEQ ID NO: 16) |
| L123Y | CACCGGAAACGGCAGTTTCTTAT AGCTATCATAGATCACGGTATG (SEQ ID NO: 17) | CATACCGTGATCTATGATAGCTAT AAGAAACTGCCGTTTCCGGTG (SEQ ID NO: 18) |
| T140K | ATATCGCCTTTCAGCACCTTCAG TTTAAAGTCCTTCGCGA (SEQ ID NO: 19) | TCGCGAAGGACTTTAAACTGAAGG TGCTGAAAGGCGATAT (SEQ ID NO: 20) |
| T140H | AATATCGCCTTTCAGCACGTGCA GTTTAAAGTCCTTCGCG (SEQ ID NO: 21) | CGCGAAGGACTTTAAACTGCACGT GCTGAAAGGCGATATT (SEQ ID NO: 22) |
| Y148P | AAAGGCGATATTGACCCGCATA AGAACGCCCG (SEQ ID NO: 23) | CGGGCGTTCTTTATGCGGGTCAAT ATCGCCTTT (SEQ ID NO: 24) |
| Y148E | AAAGGCGATATTGACGAACATA AGAACGCCCG (SEQ ID NO: 25) | CGGGCGTTCTTTATGTTCGTCAAT ATCGCCTTT (SEQ ID NO: 26) |
| I158P | CCGGTGGGCTATAAACCGACCCC GGAGGAATAT (SEQ ID NO: 27) | ATATTCCTCCGGGGTCGGTTTATA GCCCACCGG (SEQ ID NO: 28) |
| T159A | GTGGGCTATAAAATTGCGCCGGA GGAATATGCG (SEQ ID NO: 29) | CGCATATTCCTCCGGCGCAATTTT ATAGCCCAC (SEQ ID NO: 30) |
| T203E | GAAACACTTTCTTGAACTTCTTG GTCTCGATAATGTCCTTAAAGCC TTTCAGGC (SEQ ID NO: 31) | GCCTGAAAGGCTTTAAGGACATTA TCGAGACCAAGAAGTTCAAGAAA GTGTTTC (SEQ ID NO: 32) |

TABLE 1-continued

| mutation site | nucleotide sequence of forward primer (5'-3') | nucleotide sequence of reverse primer (5'-3') |
|---|---|---|
| Y224E | AGCCACCGCGATACGCCTCGCGC ACTTCTTTATCC (SEQ ID NO: 33) | GGATAAAGAAGTGCGCGAGGCGT ATCGCGGTGGCT (SEQ ID NO: 34) |
| F309S | ATTAAACGCAGCCGCAGCTATAA AGGCAACGAG (SEQ ID NO: 35) | CTCGTTGCCTTTATAGCTGCGGCT GCGTTTAAT (SEQ ID NO: 36) |
| Y310N | AAACGCAGCCGCTTTAATAAAG GCAACGAGTAC (SEQ ID NO: 37) | GTACTCGTTGCCTTTATTAAAGCG GCTGCGTTT (SEQ ID NO: 38) |
| Y310G | AAACGCAGCCGCTTTGGTAAAG GCAACGAGTAC (SEQ ID NO: 39) | GTACTCGTTGCCTTTACCAAAGCG GCTGCGTTT (SEQ ID NO: 40) |
| G320H | TACCTGAAAAGCAGCCATGGCG AAATTGCGGAT (SEQ ID NO: 41) | ATCCGCAATTTCGCCATGGCTGCT TTTCAGGTA (SEQ ID NO: 42) |
| G320E | TACCTGAAAAGCAGCGAAGGCG AAATTGCGGAT (SEQ ID NO: 43) | ATCCGCAATTTCGCCTTCGCTGCTT TTCAGGTA (SEQ ID NO: 44) |
| G320D | TACCTGAAAAGCAGCGATGGCG AAATTGCGGAT (SEQ ID NO: 45) | ATCCGCAATTTCGCCATCGCTGCT TTTCAGGTA (SEQ ID NO: 46) |
| G320C | TACCTGAAAAGCAGCTGTGGCG AAATTGGGGAT (SEQ ID NO: 47) | ATCCGCAATTTCGCCACAGCTGCT TTTCAGGTA (SEQ ID NO: 48) |
| N344R | CACTACGATCTGTACCGTGTGGA ATATATCAGC (SEQ ID NO: 49) | GCTGATATATTCCACACGGTACAG ATCGTAGTG (SEQ ID NO: 50) |
| V345E | TACGATCTGTACAACGAAGAATA TATCAGCGGC (SEQ ID NO: 51) | GCCGCTGATATATTCTTCGTTGTA CAGATCGTA (SEQ ID NO: 52) |
| Y347G | TTTAAATTTCAGGCCGCTGATAC CTTCCACGTTGTACAGATCGTAG (SEQ ID NO: 53) | CTACGATCTGTACAACGTGGAAGG TATCAGCGGCCTGAAATTTAAA (SEQ ID NO: 54) |
| V509E | ATCTACATGAAAGAGGAAGATG GCAAACTGGTT (SEQ ID NO: 55) | AACCAGTTTGCCATCTTCCTCTTTC ATGTAGAT (SEQ ID NO: 56) |
| ES15W | CATCCGGGCTGCCCCAAACCAGT TTGCCATCCACCTCTTTC (SEQ ID NO: 57) | GAAAGAGGTGGATGGCAAACTGG TTTGGGGCAGCCCGGATG (SEQ ID NO: 58) |
| E515T | GAAAGAGGTGGATGGCAAACTG GTTACGGGCAGCCCGGATG (SEQ ID NO: 59) | CATCCGGGCTGCCCGTAACCAGTT TGCCATCCACCTCTTTC (SEQ ID NO: 60) |
| E515S | GAGGTGGATGGCAAACTGGTTTC AGGCAGCCCGG (SEQ ID NO: 61) | CCGGGCTGCCTGAAACCAGTTTGC CATCCACCTC (SEQ ID NO: 62) |
| E515R | CCGGGCTGCCTCTAACCAGTTTG CCATCCACCTC (SEQ ID NO: 63) | GAGGTGGATGGCAAACTGGTTAG AGGCAGCCCGG (SEQ ID NO: 64) |
| E515N | CCGGGCTGCCATTAACCAGTTTG CCATCCACC (SEQ ID NO: 65) | GGTGGATGGCAAACTGGTTAATGG CAGCCCGG (SEQ ID NO: 66) |
| E515I | CCGGGCTGCCTATAACCAGTTTG CCATCCACCTC (SEQ ID NO: 67) | GAGGTGGATGGCAAACTGGTTATA GGCAGCCCGG (SEQ ID NO: 68) |
| E515F | CATCCGGGCTGCCGAAAACCAGT TTGCCATCCACCTCTTTC (SEQ ID NO: 69) | GAAAGAGGTGGATGGCAAACTGG TTTTCGGCAGCCCGGATG (SEQ ID NO: 70) |

TABLE 1-continued

| mutation site | nucleotide sequence of forward primer (5'-3') | nucleotide sequence of reverse primer (5'-3') |
|---|---|---|
| R96E | CATATACCACTGGCCCATCTCGC TAATAATGGTGTTATAGGTGTTC G (SEQ ID NO: 71) | CGAACACCTATAACACCATTATTA GCGAGATGGGCCAGTGGTATATG (SEQ ID NO: 72) |
| R96N | AACACCATTATTAGCAATATGGG CCAGTGGTAT (SEQ ID NO: 73) | ATACCACTGGCCCATATTGCTAAT AATGGTGTT (SEQ ID NO: 74) |
| R96A | AACACCATTATTAGCGCGATGGG CCAGTGGTAT (SEQ ID NO: 75) | ATACCACTGGCCCATCGCGCTAAT AATGGTGTT (SEQ ID NO: 76) |
| R96G | AACACCATTATTAGCGGTATGGG CCAGTGGTAT (SEQ ID NO: 77) | ATACCACTGGCCCATACCGCTAAT AATGGTGTT (SEQ ID NO: 78) |
| R96K | CATATACCACTGGCCCATCTTGC TAATAATGGTGTTATAGGTGTTC G (SEQ ID NO: 79) | CGAACACCTATAACACCATTATTA GCAAGATGGGCCAGTGGTATATG (SEQ ID NO: 80) |
| M97V | CATATACCACTGGCCCACGCGGC TAATAATGGTGT (SEQ ID NO: 81) | ACACCATTATTAGCCGCGTGGGCC AGTGGTATATG (SEQ ID NO: 82) |
| M97C | ATATCAATCATATACCACTGGCC GCAGCGGCTAATAATGGTGTTAT AGG (SEQ ID NO: 83) | CCTATAACACCATTATTAGCCGCT GCGGCCAGTGGTATATGATTGATA T (SEQ ID NO: 84) |
| M97P | ATAACACCATTATTAGCCGCCCG GGCCAGTGGTATATGATTG (SEQ ID NO: 85) | CAATCATATACCACTGGCCCGGGC GGCTAATAATGGTGTTAT (SEQ ID NO: 86) |
| M97W | CAATCATATACCACTGGCCCCAG CGGCTAATAATGGTGTTAT (SEQ ID NO: 87) | ATAACACCATTATTAGCCGCTGGG GCCAGTGGTATATGATTG (SEQ ID NO: 88) |
| M97N | CATATACCACTGGCCATTGCGGC TAATAATGGTGTTATAGG (SEQ ID NO: 89) | CCTATAACACCATTATTAGCCGCA ATGGCCAGTGGTATATG (SEQ ID NO: 90) |
| M97D | GATATCAATCATATACCACTGGC CATCGCGGCTAATAATGGTGTTA TAGGT (SEQ ID NO: 91) | ACCTATAACACCATTATTAGCCGC GATGGCCAGTGGTATATGATTGAT ATC (SEQ ID NO: 92) |
| M97E | CAATCATATACCACTGGCCCTCG CGGCTAATAATGGTGTTAT (SEQ ID NO: 93) | ATAACACCATTATTAGCCGCGAGG GCCAGTGGTATATGATTG (SEQ ID NO: 94) |
| M97Y | GATATCAATCATATACCACTGGC CATAGCGGCTAATAATGGTGTTA TAGGT (SEQ ID NO: 95) | ACCTATAACACCATTATTAGCCGC TATGGCCAGTGGTATATGATTGAT ATC (SEQ ID NO: 96) |
| M97R | TACCACTGGCCCCTGCGGCTAAT AATGGTGTTATAG (SEQ ID NO: 97) | CTATAACACCATTATTAGCCGCAG GGGCCAGTGGTA (SEQ ID NO: 98) |
| M97S | CATATACCACTGGCCGCTGCGGC TAATAATGGTGTTATAGG (SEQ ID NO: 99) | CCTATAACACCATTATTAGCCGCA GCGGCCAGTGGTATATG (SEQ ID NO: 100) |
| Q99V | CAGATATCAATCATATACCACAC GCCCATGCGGCTAATAATGG (SEQ ID NO: 101) | CCATTATTAGCCGCATGGGCGTGT GGTATATGATTGATATCTG (SEQ ID NO: 102) |
| Q99E | GATATCAATCATATACCACTCGC CCATGCGGCTAATAATG (SEQ ID NO: 103) | CATTATTAGCCGCATGGGCGAGTG GTATATGATTGATATC (SEQ ID NO: 104) |
| Q99T | ATTAGCCGCATGGGCACCTGGTA TATGATTGAT (SEQ ID NO: 105) | ATCAATCATATACCAGGTGCCCAT GCGGCTAAT (SEQ ID NO: 106) |
| L123A | CGGAAACGGCAGTTTCTTCGCGC TATCATAGATCACGGTA (SEQ ID NO: 107) | TACCGTGATCTATGATAGCGCGAA GAAACTGCCGTTTCCG (SEQ ID NO: 108) |

TABLE 1-continued

| mutation site | nucleotide sequence of forward primer (5'-3') | nucleotide sequence of reverse primer (5'-3') |
|---|---|---|
| L123C | CACCGGAAACGGCAGTTTCTTGC AGCTATCATAGATCACGGTATG (SEQ ID NO: 109) | CATACCGTGATCTATGATAGCTGC AAGAAACTGCCGTTTCCGGTG (SEQ ID NO: 110) |
| L123Q | GAAACGGCAGTTTCTTCTGGCTA TCATAGATCACG (SEQ ID NO: 111) | CGTGATCTATGATAGCCAGAAGAA ACTGCCGTTTC (SEQ ID NO: 112) |
| L123M | GAAACGGCAGTTTCTTCATGCTA TCATAGATCACGGT (SEQ ID NO: 113) | ACCGTGATCTATGATAGCATGAAG AAACTGCCGTTTC (SEQ ID NO: 114) |
| L123N | CACCGGAAACGGCAGTTTCTTAT TGCTATCATAGATCACGGTATG (SEQ ID NO: 115) | CATACCGTGATCTATGATAGCAAT AAGAAACTGCCGTTTCCGGTG (SEQ ID NO: 116) |
| Q171E | ACATCAAGAACGACATCGAGAT TATTGCGGAAGCG (SEQ ID NO: 117) | CGCTTCCGCAATAATCTCGATGTC GTTCTTGATGT (SEQ ID NO: 118) |
| Q171K | ATCAAGAACGACATCAAAATTAT TGCGGAAGCG (SEQ ID NO: 119) | CGCTTCCGCAATAATTTTGATGTC GTTCTTGAT (SEQ ID NO: 120) |
| T204K | AAGGACATTATCACCAAGAAGA AGTTCAAGAAA (SEQ ID NO: 121) | TTTCTTGAACTTCTTCTTGGTGATA ATGTCCTT (SEQ ID NO: 122) |
| T213K | AAGAAAGTGTTTCCGAAACTGA GCCTGGGCCTG (SEQ ID NO: 123) | CAGGCCCAGGCTCAGTTTCGGAAA CACTTTCTT (SEQ ID NO: 124) |
| G217K | CCGACCCTGAGCCTGAAACTGGA TAAAGAAGTG (SEQ ID NO: 125) | CACTTCTTTATCCAGTTTCAGGCTC AGGGTCGG (SEQ ID NO: 126) |
| V250I | GGATACAGGCTGTTTATATCAAA CACCATGCCTTCGCCAATTT (SEQ ID NO: 127) | AAATTGGCGAAGGCATGGTGTTTG ATATAAACAGCCTGTATCC (SEQ ID NO: 128) |
| V270R | TATGGTGAACCGATTCGTTTTGA AGGCAAGTAT (SEQ ID NO: 129) | ATACTTGCCTTCAAAACGAATCGG TTCACCATA (SEQ ID NO: 130) |
| N344K | CACTACGATCTGTACAAAGTGGA ATATATCAGC (SEQ ID NO: 131) | GCTGATATATTCCACTTTGTACAG ATCGTAGTG (SEQ ID NO: 132) |
| Y369D | ATCGACAAGTGGACCGATATTAA AACCACCAGC (SEQ ID NO: 133) | GCTGGTGGTTTTAATATCGGTCCA CTTGTCGAT (SEQ ID NO: 134) |
| Y369N | ATCGACAAGTGGACCAATATTAA AACCACCAGC (SEQ ID NO: 135) | GCTGGTGGTTTTAATATTGGTCCA CTTGTCGAT (SEQ ID NO: 136) |
| K402L | CTTTCAGATACGGCACTAAGCCG GTAACATCCGGGT (SEQ ID NO: 137) | ACCCGGATGTTACCGGCTTAGTGC CGTATCTGAAAG (SEQ ID NO: 138) |
| L416A | GCGCTGGGCTTTCGTGCGGGCGA AGAGGAAACC (SEQ ID NO: 139) | GGTTTCCTCTTCGCCCGCACGAAA GCCCAGCGC (SEQ ID NO: 140) |
| E515F | CATCCGGGCTGCCGAAAACCAGT TTGCCATCCACCTCTTTC (SEQ ID NO: 141) | GAAAGAGGTGGATGGCAAACTGG TTTTCGGCAGCCCGGATG (SEQ ID NO: 142) |
| E515H | CCGGGCTGCCATGAACCAGTTTG CCATCCACC (SEQ ID NO: 143) | GGTGGATGGCAAACTGGTTCATGG CAGCCCGG (SEQ ID NO: 144) |
| E515Q | CCGGGCTGCCCTGAACCAGTTTG CCATCCACC (SEQ ID NO: 145) | GGTGGATGGCAAACTGGTTCAGG GCAGCCCGG (SEQ ID NO: 146) |

TABLE 1-continued

| mutation site | nucleotide sequence of forward primer (5'-3') | nucleotide sequence of reverse primer (5'-3') |
|---|---|---|
| E515T | GAAAGAGGTGGATGGCAAACTG GTTACGGGCAGCCCGGATG (SEQ ID NO: 147) | CATCCGGGCTGCCCGTAACCAGTT TGCCATCCACCTCTTTC (SEQ ID NO: 148) |
| I524V | GATGATTATACCGATGTGAAGTT CAGCGTGAAA (SEQ ID NO: 149) | TTTCACGCTGAACTTCACATCGGT ATAATCATC (SEQ ID NO: 150) |

1.2.2 PCR amplification was proformed with the PCR reaction system for the site-directed mutagenesis, and a PCR amplified product was obtained.

The reaction program was set as (i) 95° C. for 3 min; (ii) 95° C. for 30 s, 53° C. for 30 s, 68° C. for 8 min, where (ii) was proformed for 19 cycles; and (iii) 4° C. for hold.

1.2.3 The PCR amplified product was digested by DpnI enzyme and transformed into *E. coli* DH5a competent cells, followed by spreading on Luria-Bertani (LB) medium plates containing kanamycin and culturing at 37° C. overnight. Single clones were picked and plasmids therein were extracted.

1.2.4 The plasmids extracted at step 1.2.3 were sequenced individually. Based on the sequencing results, several recombinant plasmids each with a site mutation in the gene encoding the Phi29 DNA polymerase were obtained, for encoding different fusion proteins respectively (i.e. recombinant phi29 DNA polymerase).

The fusion proteins encoded by part of recombinant plasmids are shown in Table 2.

TABLE 2

| Name of recombinant plasmid | Encoded fusion protein | Difference with the fusion protein 1 |
|---|---|---|
| recombinant plasmid pET28a-T17P | fusion protein 2 | T at position 37 was substituted with P |
| recombinant plasmid pET28a-M97Y | fusion protein 3 | M at position 117 was substituted with Y |
| recombinant plasmid pET28a-M97S | fusion protein 4 | M at position 117 was substituted with S |
| recombinant plasmid pET28a-M97R | fusion protein 5 | M at position 117 was substituted with R |
| recombinant plasmid pET28a-M97Q | fusion protein 6 | M at position 117 was substituted with Q |
| recombinant plasmid pET28a-M97G | fusion protein 7 | M at position 117 was substituted with G |
| recombinant plasmid pET28a-L123Y | fusion protein 8 | L at position 143 was substituted with Y |
| recombinant plasmid pET28a-T140K | fusion protein 9 | T at position 160 was substituted with K |
| recombinant plasmid pET28a-T140H | fusion protein 10 | T at position 160 was substituted with H |
| recombinant plasmid pET28a-Y148P | fusion protein 11 | Y at position 168 was substituted with P |
| recombinant plasmid pET28a-Y148E | fusion protein 12 | Y at position 168 was substituted with E |
| recombinant plasmid pET28a-I158P | fusion protein 13 | I at position 178 was substituted with P |
| recombinant plasmid pET28a-T159A | fusion protein 14 | T at position 179 was substituted with A |
| recombinant plasmid pET28a-T203E | fusion protein 15 | T at position 223 was substituted with E |
| recombinant plasmid pET28a-Y224E | fusion protein 16 | Y at position 244 was substituted with E |
| recombinant plasmid pET28a-F309S | fusion protein 17 | F at position 329 was substituted with S |
| recombinant plasmid pET28a-Y310N | fusion protein 18 | Y at position 330 was substituted with N |

TABLE 2-continued

| Name of recombinant plasmid | Encoded fusion protein | Difference with the fusion protein 1 |
|---|---|---|
| recombinant plasmid pET28a-Y310G | fusion protein 19 | Y at position 330 was substituted with G |
| recombinant plasmid pET28a-G320H | fusion protein 20 | G at position 340 was substituted with H |
| recombinant plasmid pET28a-G320E | fusion protein 21 | G at position 340 was substituted with E |
| recombinant plasmid pET28a-G320D | fusion protein 22 | G at position 340 was substituted with D |
| recombinant plasmid pET28a-G320C | fusion protein 23 | G at position 340 was substituted with C |
| recombinant plasmid pET28a-N344R | fusion protein 24 | N at position 364 was substituted with R |
| recombinant plasmid pET28a-V345E | fusion protein 25 | V at position 365 was substituted with E |
| recombinant plasmid pET28a-Y347G | fusion protein 26 | Y at position 367 was substituted with G |
| recombinant plasmid pET28a-V509E | fusion protein 27 | V at position 529 was substituted with E |
| recombinant plasmid pET28a-E515W | fusion protein 28 | E at position 535 was substituted with W |
| recombinant plasmid pET28a-E515T | fusion protein 29 | E at position 535 was substituted with T |
| recombinant plasmid pET28a-E515S | fusion protein 30 | E at position 535 was substituted with S |
| recombinant plasmid pET28a-E515R | fusion protein 31 | E at position 535 was substituted with R |
| recombinant plasmid pET28a-E515N | fusion protein 32 | E at position 535 was substituted with N |
| recombinant plasmid pET28a-E515I | fusion protein 33 | E at position 535 was substituted with I |
| recombinant plasmid pET28a-E515F | fusion protein 34 | E at position 535 was substituted with F |
| recombinant plasmid pET28a-R96E | fusion protein 35 | R at position 116 was substituted with E |
| recombinant plasmid pET28a-R96N | fusion protein 36 | R at position 116 was substituted with N |
| recombinant plasmid pET28a-R96S | fusion protein 37 | R at position 116 was substituted with S |
| recombinant plasmid pET28a-R96A | fusion protein 38 | R at position 116 was substituted with A |
| recombinant plasmid pET28a-R96G | fusion protein 39 | R at position 116 was substituted with G |
| recombinant plasmid pET28a-R96K | fusion protein 40 | R at position 116 was substituted with K |
| recombinant plasmid pET28a-M97C | fusion protein 41 | M at position 117 was substituted with C |
| recombinant plasmid pET28a-M97P | fusion protein 42 | M at position 117 was substituted with P |
| recombinant plasmid pET28a-M97V | fusion protein 43 | M at position 117 was substituted with V |
| recombinant plasmid pET28a-M97W | fusion protein 44 | M at position 117 was substituted with W |
| recombinant plasmid pET28a-M97N | fusion protein 45 | M at position 117 was substituted with N |
| recombinant plasmid pET28a-M97D | fusion protein 46 | M at position 117 was substituted with D |
| recombinant plasmid pET28a-M97E | fusion protein 47 | M at position 117 was substituted with E |
| recombinant plasmid pET28a-Q99V | fusion protein 48 | Q at position 119 was substituted with V |

TABLE 2-continued

| Name of recombinant plasmid | Encoded fusion protein | Difference with the fusion protein 1 |
|---|---|---|
| recombinant plasmid pET28a-Q99E | fusion protein 49 | Q at position 119 was substituted with E |
| recombinant plasmid pET28a-Q99T | fusion protein 50 | Q at position 119 was substituted with T |
| recombinant plasmid pET28a-L123A | fusion protein 51 | L at position 143 was substituted with A |
| recombinant plasmid pET28a-L123C | fusion protein 52 | L at position 143 was substituted with C |
| recombinant plasmid pET28a-L123Q | fusion protein 53 | L at position 143 was substituted with Q |
| recombinant plasmid pET28a-L123M | fusion protein 54 | L at position 143 was substituted with M |
| recombinant plasmid pET28a-L123N | fusion protein 55 | L at position 143 was substituted with N |
| recombinant plasmid pET28a-Q171E | fusion protein 56 | Q at position 191 was substituted with E |
| recombinant plasmid pET28a-Q171K | fusion protein 57 | Q at position 191 was substituted with K |
| recombinant plasmid pET28a-T204K | fusion protein 58 | T at position 224 was substituted with K |
| recombinant plasmid pET28a-T213K | fusion protein 59 | T at position 233 was substituted with K |
| recombinant plasmid pET28a-G217K | fusion protein 60 | G at position 237 was substituted with K |
| recombinant plasmid pET28a-V250I | fusion protein 61 | V at position 270 was substituted with I |
| recombinant plasmid pET28a-V270R | fusion protein 62 | V at position 290 was substituted with R |
| recombinant plasmid pET28a-N344K | fusion protein 63 | N at position 364 was substituted with K |
| recombinant plasmid pET28a-Y369D | fusion protein 64 | Y at position 389 was substituted with D |
| recombinant plasmid pET28a-Y369N | fusion protein 65 | Y at position 389 was substituted with N |
| recombinant plasmid pET28a-K402L | fusion protein 66 | K at position 422 was substituted with L |
| recombinant plasmid pET28a-L416A | fusion protein 67 | L at position 436 was substituted with A |
| recombinant plasmid pET28a-E515H | fusion protein 68 | E at position 535 was substituted with H |
| recombinant plasmid pET28a-E515Q | fusion protein 69 | E at position 535 was substituted with Q |
| recombinant plasmid pET28a-E515T | fusion protein 70 | E at position 535 was substituted with T |
| recombinant plasmid pET28a-I524V | fusion protein 71 | I at position 544 was substituted with V |

1.3 Preparation of the Crude Recombinant Phi29 DNA Polymerase

A method for the preparing the crude recombinant phi29 DNA polymerase was as follows.

1.3.1 The recombinant plasmid pET28a-WT was transformed into *E. coli* BL21 (DE3) to obtain a recombinant bacterium named as BL21 (DE3)-WT.

1.3.2 Single clones of BL21 (DE3)-WT were picked and transferred into 5 ml LB fluid medium containing 50 μg/ml kanamycin, and cultured under shaking at 37° C. and 200 rpm for 12 h to obtain cultured bacteria solution.

1.3.3 The cultured bacteria solution was transferred into 1.5 L LB fluid medium containing 50 μg/ml kanamycin by a volume ratio of 1:100, followed by culturing under shaking at 37° C. and 200 rpm to $OD_{600\ nm}$ to 0.6. Then, Isopropyl-β-D-thiogalactopyranoside (IPTG) was added to a final concentration of 0.5 mM, and the bacteria were cultured under shaking at 16° C. and 200 rpm for 12 h, followed by centrifuging at 4° C. and 8000 rpm for 10 min to collect the bacterial pellet.

1.3.4 After step 1.3.3, the bacterial pellet was resuspended with the affinity solution A, then incubated on ice for 30 min, and the bacteria were ultrasonically broken in ice-water bath by a Φ6 probe of Ningbo Xinzhi ultrasonic breaker with 40% ultrasonic power, where the cycle program was set for breaking for 2 s, stopping for 3 s and the total program was for 30 min, followed by centrifuging at 4° C. and 15000 rpm for 30 min, and the supernatant was collected.

1.3.5 After step 4, the supernatant was purified rapidly with affinity chromatography, followed by dialyzing, where solutes and concentrations thereof in a dialysis buffer were 200 mM of KCl, 0.2 mM of EDTA, 5% Glycerol and 20 mM of Tris-HCl; solvent of the buffer was water; pH value was 7.5; and the temperature was 25° C., and thus a crude recombinant phi29 DNA polymerase 1 was obtained.

Following the above steps, the material of recombinant plasmid pET28a-WT was individually replaced with the recombinant plasmid pET28a-T17P, recombinant plasmid pET28a-M97Y, recombinant plasmid pET28a-M97S, recombinant plasmid pET28a-M97R, recombinant plasmid pET28a-M97Q, recombinant plasmid pET28a-M97G, Plasmid pET28a-L123Y, recombinant plasmid pET28a-T140K, recombinant plasmid pET28a-T140H, recombinant plasmid pET28a-Y148P, recombinant plasmid pET28a-Y148E, recombinant plasmid pET28a-1158P, recombinant plasmid pET28a-T159A, recombinant plasmid pET28a-T203E, recombinant plasmid pET28a-Y224E, recombinant plasmid pET28a-F309S, recombinant plasmid pET28a-Y310N, recombinant plasmid pET28a-Y310G, recombinant plasmid pET28a-G320H, recombinant plasmid pET28a-G320E, recombinant plasmid pET28a-G320D, recombinant plasmid pET28a-G320C, recombinant plasmid pET28a-N344R, recombinant plasmid pET28a-V345E, recombinant plasmid pET28a-Y347G, recombinant plasmid pET28a-V509E, recombinant plasmid pET28a-E515W, recombinant plasmid pET28a-E515T, recombinant plasmid pET28a-E515S, recombinant plasmid pET28a-E515R, recombinant plasmid pET28a-E515N, recombinant plasmid Plasmid pET28a-E515I, recombinant plasmid pET28a-E515F, recombinant plasmid pET28a-R96E, recombinant plasmid pET28a-R96N, recombinant plasmid pET28a-R96S, recombinant plasmid pET28a-R96A, recombinant plasmid pET28a-R96G, recombinant plasmid pET28a-R96K, recombinant plasmid pET28a-M97C, recombinant plasmid pET28a-M97P, recombinant plasmid pET28a-M97V, recombinant plasmid pET28a-M97W, recombinant plasmid pET28a-M97N, recombinant plasmid pET28a-M97E, recombinant plasmid pET28a-Q99V, recombinant plasmid pET28a-Q99E, recombinant plasmid pET28a-Q99T, recombinant plasmid pET28a-L123A, recombinant plasmid pET28a-L123C, recombinant plasmid pET28a-L123Q, recombinant plasmid pET28a-L123M, recombinant plasmid pET28a-L123N, recombinant plasmid pET28a-Q171E, recombinant plasmid pET28a-Q171K, recombinant plasmid Plasmid pET28a-T204K, recombinant plasmid pET28a-T213K, recombinant plasmid pET28a-G217K, recombinant plasmid pET28a-V250I, recombinant plasmid pET28a-V270R, recombinant plasmid pET28a-N344K, recombinant plasmid pET28a-Y369D, recombinant plasmid pET28a-Y369N, recombinant plasmid pET28a-K402L, recombinant plasmid pET28a-L416A, recombinant plasmid pET28a-E515H, recombinant plasmid pET28a-E515Q, recombinant plasmid pET28a-E515T and recombinant plasmid pET28a-1524V, where other steps were all unchanged, and thus crude recombinant phi29 DNA polymerases 2 to 71 were obtained sequentially.

Example 2: Assay on Stability of the Crude Recombinant Phi29 DNA Polymerases Prepared in Example 1

The 71 crude recombinant phi29 DNA polymerases prepared in Example 1 and the dialysis buffer were assayed for the Tm value with a protein thermal shift assay kit (Life Technologies) individually. Specifically, a program was set and a reaction buffer was prepared according to the instructions of the protein thermal shift studies user guide. After the program was completed, the experimental results were input to protein thermal shift software for analysis, thereby obtaining the Tm values of each sample.

The recombinant phi29 DNA polymerase 1 was set as a positive control.

The dialysis buffer was set as a negative control.

Each sample was repeated in quadruplicate and averaged. Part of results is shown in Table 3. The results show that the crude recombinant phi29 DNA polymerases 2 to 34 each are of an increased Tm value to a certain degree as compared with the crude recombinant phi29 DNA polymerase 1, indicating that the crude recombinant phi29 DNA polymerases 2 to 34 exhibit an improved stability to a certain degree.

TABLE 3

| Crude recombinant phi29 DNA polymerase | Tm (° C.) | Crude recombinant phi29 DNA polymerase | Tm (° C.) |
| --- | --- | --- | --- |
| Crude recombinant phi29 DNA polymerase 26 | 49.60677 | Crude recombinant phi29 DNA polymerase 6 | 48.22635 |
| Crude recombinant phi29 DNA polymerase 18 | 48.38237 | Crude recombinant phi29 DNA polymerase 1 | 48.18446 |
| Crude recombinant phi29 DNA polymerase 19 | 48.24233 | Crude recombinant phi29 DNA polymerase 7 | 48.2925 |
| Crude recombinant phi29 DNA polymerase 16 | 48.91264 | Crude recombinant phi29 DNA polymerase 8 | 49.04076 |
| Crude recombinant phi29 DNA polymerase 11 | 48.54876 | Crude recombinant phi29 DNA polymerase 34 | 49.07857 |
| Crude recombinant phi29 DNA polymerase 12 | 48.66696 | Crude recombinant phi29 DNA polymerase 13 | 48.20793 |
| Crude recombinant phi29 DNA polymerase 27 | 48.87052 | Crude recombinant phi29 DNA polymerase 20 | 48.22497 |
| Crude recombinant phi29 DNA polymerase 25 | 48.88358 | Crude recombinant phi29 DNA polymerase 21 | 48.21473 |
| Crude recombinant phi29 DNA polymerase 15 | 48.49379 | Crude recombinant phi29 DNA polymerase 22 | 48.61902 |
| Crude recombinant phi29 DNA polymerase 2 | 48.61609 | Crude recombinant phi29 DNA polymerase 23 | 48.46351 |
| Crude recombinant phi29 DNA polymerase 14 | 49.30812 | Crude recombinant phi29 DNA polymerase 17 | 49.03835 |
| Crude recombinant phi29 DNA polymerase 9 | 48.55235 | Crude recombinant phi29 DNA polymerase 28 | 48.96379 |
| Crude recombinant phi29 DNA polymerase 10 | 48.91756 | Crude recombinant phi29 DNA polymerase 29 | 48.24366 |
| Crude recombinant phi29 DNA polymerase 24 | 48.27392 | Crude recombinant phi29 DNA polymerase 30 | 48.68517 |
| Crude recombinant phi29 DNA polymerase 3 | 49.18874 | Crude recombinant phi29 DNA polymerase 31 | 48.68651 |
| Crude recombinant phi29 DNA polymerase 5 | 49.12807 | Crude recombinant phi29 DNA polymerase 32 | 48.88325 |
| Crude recombinant phi29 DNA polymerase 4 | 49.45142 | Crude recombinant phi29 DNA polymerase 33 | 48.23149 |

Example 3: Assay on Specific Enzyme Activity of
the Crude Recombinant Phi29 DNA Polymerases
Prepared in Example 1

Each of the 71 crude recombinant phi29 DNA polymerases prepared in Example 1 was subjected to the assay
on specific enzyme activity.

3.1 The crude recombinant phi29 DNA polymerases were
assayed for protein concentration with a BCA kit, followed
by diluting with the dialysis buffer, thereby obtaining
respective diluents of the recombinant phi29 DNA poly-
merases with a concertation of 5 μg/ml.

Solutes and concentrations thereof in the dialysis buffer
were 20 mM of Tris-HCl, 200 mM of KCl, 2 mM of DTT,
0.2 mM of EDTA and 5% Glycerol; and solvent was water;
and pH value was 7.4.

3.2 A reaction mixture was prepared. The reaction mixture
was in a volume of 80.8 μl, including DTT, (NH$_4$)$_2$SO$_4$,
MgCl$_2$, dNTP Mixture, RCA Primer (i.e., Ad153 make DNB
primer, the product of Invitrogen, Cat. No. R082), 6 ng of
single-stranded circular DNA template 153Ad ssDNA and
50 mM of Tris-HCl buffer with pH7.5. In the reaction
mixture, the concentration of DTT was 4 mM, the concen-
tration of (NH$_4$)$_2$SO$_4$ was 10 mM, the concentration of
MgCl$_2$ was 10 mM, the concentration of dNTP Mixture was
50 nM and the concentration of RCA Primer was 2 μM.

3.3 The reaction mixture was placed in a PCR amplifier
for primer-template hybridization, and the program was set
as follows: 95° C. for 1 min, 65° C. for 1 min, 40° C. for 1
min, and the temperature of the hot cover was set at 102° C.

When the temperature reached 4° C., the PCR tube was
taken out and placed on ice, added with 1 μl of the diluent
of the recombinant phi29 DNA polymerase, followed by
shaking and mixing with a vortex shaker. With a temporary
centrifugation, the PCR tube was placed in the PCR ampli-
fier for reaction, and the reaction conditions were 30° C. for
60 min and the temperature of the hot cover was set at 65°
C. After the reaction was completed, 5 μl of EDTA solution
at a concentration of 0.5 M was added to stop the reaction.
After shaking and mixing, a reaction product was obtaining.

3.4 The reaction product obtained in step 3.3 was assayed
for concentration with the Qubit fluorometer 3.0, according
to the instructions of the Qubit ssDNA assay kit. 1U enzyme
activity is defined as the amount of enzyme required for
producing DNB based on 10 nmol dNTP at 30° C. for 60
min. The the crude recombinant phi29 DNA polymerases
were further assayed for specific enzyme activity.

Part of the results is shown in Table 4. The results show
that the crude recombinant phi29 DNA polymerase 3, the
crude recombinant phi29 DNA polymerase 4, the crude
recombinant phi29 DNA polymerase 5 and the crude recom-
binant phi29 DNA polymerases 34 to 71 each are of an
increased specific enzyme activity to a certain degree as
compared with the crude recombinant phi29 DNA poly-
merase 1, indicating that the crude recombinant phi29 DNA
polymerase 3, the crude recombinant phi29 DNA poly-
merase 4, the crude recombinant phi29 10 DNA polymerase
5 and the crude recombinant phi29 DNA polymerases 34 to
71 each exhibit an improved DNA polymerase activity to a
certain degree.

TABLE 4

| Crude recombinant phi29 DNA polymerase | Specific enzyme activity (U/μg) | Crude recombinant phi29 DNA polymerase | Specific enzyme activity (U/μg) |
|---|---|---|---|
| Crude recombinant phi29 DNA polymerase 5 | 27.86966 | Crude recombinant phi29 DNA polymerase 48 | 25.01471 |
| Crude recombinant phi29 DNA polymerase 3 | 37.38322 | Crude recombinant phi29 DNA polymerase 41 | 37.27798 |
| Crude recombinant phi29 DNA polymerase 61 | 27.97547 | Crude recombinant phi29 DNA polymerase 42 | 39.54949 |
| Crude recombinant phi29 DNA polymerase 66 | 32.28242 | Crude recombinant phi29 DNA polymerase 43 | 29.82229 |
| Crude recombinant phi29 DNA polymerase 35 | 18.99764 | Crude recombinant phi29 DNA polymerase 44 | 25.93127 |
| Crude recombinant phi29 DNA polymerase 56 | 29.17352 | Crude recombinant phi29 DNA polymerase 45 | 30.63974 |
| Crude recombinant phi29 DNA polymerase 58 | 27.19059 | Crude recombinant phi29 DNA polymerase 46 | 56.83838 |
| Crude recombinant phi29 DNA polymerase 59 | 27.57224 | Crude recombinant phi29 DNA polymerase 47 | 42.18217 |
| Crude recombinant phi29 DNA polymerase 64 | 26.18703 | Crude recombinant phi29 DNA polymerase 51 | 31.52057 |
| Crude recombinant phi29 DNA polymerase 63 | 28.0683 | Crude recombinant phi29 DNA polymerase 52 | 35.26901 |
| Crude recombinant phi29 DNA polymerase 36 | 21.52907 | Crude recombinant phi29 DNA polymerase 53 | 64.68987 |
| Crude recombinant phi29 DNA polymerase 57 | 22.02841 | Crude recombinant phi29 DNA polymerase 54 | 23.80637 |
| Crude recombinant phi29 DNA polymerase 60 | 24.79935 | Crude recombinant phi29 DNA polymerase 55 | 34.63575 |
| Crude recombinant phi29 DNA polymerase 65 | 28.91615 | Crude recombinant phi29 DNA polymerase 50 | 25.04765 |
| Crude recombinant phi29 DNA polymerase 67 | 33.68722 | Crude recombinant phi29 DNA polymerase 68 | 20.20621 |
| Crude recombinant phi29 DNA polymerase 71 | 22.68731 | Crude recombinant phi29 DNA polymerase 38 | 16.16717 |
| Crude recombinant phi29 DNA polymerase 34 | 24.50766 | Crude recombinant phi29 DNA polymerase 39 | 18.00866 |
| Crude recombinant phi29 DNA polymerase 4 | 19.88544 | Crude recombinant phi29 DNA polymerase 40 | 19.72106 |

TABLE 4-continued

| Crude recombinant phi29 DNA polymerase | Specific enzyme activity (U/μg) | Crude recombinant phi29 DNA polymerase | Specific enzyme activity (U/μg) |
| --- | --- | --- | --- |
| Crude recombinant phi29 DNA polymerase 62 | 19.72727 | Crude recombinant phi29 DNA polymerase 49 | 16.17894 |
| Crude recombinant phi29 DNA polymerase 1 | 13.88 | Crude recombinant phi29 DNA polymerase 69 | 17.54294 |
| Crude recombinant phi29 DNA polymerase 37 | 39.47822 | Crude recombinant phi29 DNA polymerase 70 | 69.588 |

Example 4: Preparation of a Phi29 DNA Polymerase with Combined Mutations And Assay on the Stability and Specific Enzyme Activity 4.1 Construction of a Recombinant Phi29 DNA Polymerase (i.e., the Phi29 DNA Polymerase with Combined Mutations)

The phi29 DNA polymerase with combined mutations were constructed by a DNA shuffling method or multi-site directed mutagenesis, based on the mutant sites provided in Example 1 and the known mutant sites disclosed in the literature.

The specific steps of the DNA shuffling method were as follows.

4.1.1.1 The template for shuffling was amplified with PCR (forward primer: 5'-CTGGTGCCGCGCGGCAGC-CATATG-3', SEQ ID NO: 151; reverse primer: 5'-CTCGAATTCGGATCCTCACTTGA-3', SEQ ID NO: 152). The PCR product was then recovered via cutting the gel.

4.1.1.2 A digestion reaction with DNase I enzyme was performed according to the steps shown in Table 5.

TABLE 5

| | Reagent | Volume (μl) | Conditions |
| --- | --- | --- | --- |
| Step 1 | 10 × DNaseI buffer | 5.0 | 15 min 15° C. (equilibrium) |
| | DNA1 (concertration at about 40 ng/μl) | 22.5 (concertration at about 900 ng/μl) | |
| | DNA2 (concertration at about 40 ng/μl) | 22.5 (concertration at about 900 ng/μl) | |
| Step 2 | (0.4 U/μL) DNaseI | 0.75 (0.3 U) | 1.5 min 15° C. (reacting) |
| Step 3 | 0.5M EDTA | 0.5 | 90° C. 10 min (stopping and melting) |

4.1.1.3 After the step 4.1.1.2, the digested DNA fragments were recovered with M280 magnetic beads, then washed with 75% (v/v) ethanol aqueous solution twice, and dissolved with ddH₂O.

4.1.1.4 After the step 4.1.1.3, the fragmented DNA fragments were subjected to shuffling recombination with PCR. The reaction system is shown in Table 6.

TABLE 6

| Reagent | Volume (μl) |
| --- | --- |
| ddH₂O | (21.5-DNA) |
| DNA | 0.25/0.5/1.0 |
| 10 × pfu buffer | 2.5 |
| 10 mM dNTP | 0.5 |
| Pfu polymerase | 0.5 |

The reaction program was set as: (i) 95° C. for 3 min; (ii) 95° C. for 30 s, 65° C. for 30 s, 72° C. for 1 min, and (ii) was proformed for 45 cycles; and (iii) 72° C. for 3 min; and (iv) 4° C. for hold.

4.1.1.5 After the step 4.1.1.4, enrichment by a second amplification was performed by taking the recombined fragments as the template.

The reaction system is shown in Table 7.

TABLE 7

| Reagent | Volume (μl) |
| --- | --- |
| DNA | 2.5 |
| ddH₂O | 18.0 |
| 10 × pfu buffer | 2.5 |
| 10 mM dNTP | 0.5 |
| 10 μM Primer 1 (mix of the forward primers in Table 2) | 0.5 |
| 10 μM Primer 2 (mix of the reverse primers in Table 2) | 0.5 |
| 2.5 U/μLPfu polymerase | 0.5 |

The reaction program was set as: (i) 95° C. for 3 min; (ii) 94° C. for 30 s, 60° C. for 30 s, 72° C. for 1 min and 40 s, and (ii) was proformed for 60 cycles; and (iii) 72° C. for 7 min.

With the construction of a mutant with 5 mutation sites as an example, the specific steps of the multi-site directed mutagenesis were as follows.

4.1.2.1 Primer design: the mutation site was designed in the middle of the primer flank by about 15 nt, and a pair of reversely complementary primers was designed for each mutation site.

4.1.2.2 Preparation of the reaction system: the reaction system was in a volume of 25 μl, including 12.5 μL of 2×KAPA HiFi HS Ready Mix, 3.5 μL of FW primer at a concentration of 2 μM which was a mix of 5 forward primers in total where each forward primer was accounted for 0.7 μl; 3.5 μL RE primer at a concentration of 2 μM which was a mix of 5 reverse primers in total where each reverse primer was accounted for 0.7 μl; 75 ng of the template and H₂O.

4.1.2.3 PCR amplification was proformed with the PCR reaction system above.

The reaction program was set as: (i) 95° C. for 3 min; (ii) 98° C. for 20 s, 65° C. for 15 s, 72° C. for 7 min, and (ii) was proformed for 19 cycles; (iii) 72° C. for 10 min; and (iv) 12° C. for hold.

4.1.2.4 After the step 4.1.2.3, the PCR product was added with 1 μL of dpnI enzyme for digestion for 2 h at 37° C., then transformed into E. coli DH5a competent cells, followed by spreading on medium plates and culturing at 37° C. overnight. Single clones were picked and plasmids therein were extracted for sequencing.

4.2 High-Throughput Screening of the Phi29 DNA Polymerase with Combined Mutations Constructed in Example 1

The phi29 DNA polymerase with combined mutations constructed in Example 1 was subjected to high-throughput screening by the isothermal compartmentalization self-replication (iCSR). Similar to the compartmentalization self-replication (CSR) where a plasmid for the phi29 DNA polymerase is self-replicated by means of its own activity of strand displacement, the recombinant phi29 DNA polymerase with higher activity was enriched through several rounds of screenings based on different recombinant phi29 DNA polymerases with different activities producing different amounts of amplified DNA. Specific steps performed were as follows.

4.2.1 Primer Design 3 pairs of primers were required during the whole process, where a primer pair for iCSR was used for the amplification in the iCSR process, and the 3' end of the primer pair for iCSR was thio-modified to prevent digestion by the exonuclease in the cell; and primer pairs for Insertion and vector amplification were used for amplification of an insert and a template in in-fusion reactions, respectively.

The primer pair for iCSR included Primer 1 (5'-TT-GAGGCCGTTGAGCACC-3', SEQ ID NO: 153) with thio-modification at the 3' end, and Primer 2 (5'-CCGGA-TATAGTTCCTCCTTTCAG-3', SEQ ID NO: 154) with thio-modification at the 3' end.

The primer pair for Insertion included Primer 3 (5'-AATGTATAGCTGCGACTTTGAAACCA-3', SEQ ID NO: 155) and Primer 4 (5'-TAGAGGCCCCAAGGGGTTAT-3', SEQ ID NO: 156).

The primer pair for vector amplification included Primer 5 (5'-ATAACCCCTTGGGGCCTCTA-3', SEQ ID NO: 157) and Primer 6 (5'-TGGTTTCAAAGTCGCAGCTATACAT-3', SEQ ID NO: 158).

4.2.2 Cell Transformation and Protein Expression

The constracted library of the recombinant phi29 DNA polymerases was transformed into *E. coli* BL21 competent cells, and the cells incubated at 37° C. were transferred into 2 ml LB fluid medium containing kanamycin directly without spreading on the medium plate, followed by culturing at 37° C. overnight. On the second day, the LB fluid medium containing the cells were transferred into fresh LB liquid medium containing kanamycin at a ratio of 1:200 and cultured at 37° C. for 3 h, and then IPTG was added to a final concentration of 0.5 mM to induce the cells at 16° C. overnight.

4.2.3 Preparation of a Reaction System of iCSR 4.2.3.1 Preparation of a reaction buffer: the reaction buffer was in a volume of 2 ml, including 200 μL of 10×phi29 reaction buffer, 40 μL of 500 μM Exo-resistant primer mix, 60 μL of 10 μM primer 1, 60 μL of 10 μM primer 2, 40 μL of 25 mM dNTPmix and 1600 μL of NFH$_2$O.

4.2.3.2 Preparation of cells a. 0.45 mL of 1×phi29 reaction buffer was mixed with 0.05 mL of lysozyme (10 mg/mL), followed by preheating in metal bath at 30° C., thereby obtaining a cell lysis buffer.

b. Assay of an OD value and Calculation of a final dilution volume

The the *E. coli* cells were assayed for the OD value. The number of cells=OD×8×10$^8$×2=16×OD×10$^8$, estimated based on that the concentration was 8×10$^8$ cells/mL when OD=1, the dilution volume was set as VmL.

Assuming that the diameter of a microdroplet generated was about 21 μm, the volume of a single microdroplet was 5 μL, and the volume of the bacterial channel was 2.5 μL according to the same flow rate in the bacterial channel and the buffer channel.

$$\lambda = 16 \times OD \times 10^8 \, \text{cells/VmL} \times 2.5 \text{ pL} =$$

$$16 \times 2.5 \times OD \times 10^8 \times 10^{-9}/V = 4 \times OD/V$$

If λ=0.2, there was 1% of the microdroplets containing two single cells while 16% of the microdroplets containing one single cell, and V=20×OD.

c. Cell Preparation

The induced *E. coli* cells were centrifuged at 12,000 rpm for 1 min with supernatant discard. The pellet was resuspended with 1 mL of 1×phi29 reaction buffer and washed twice, then centrifuged at 12,000 rpm for 1 min, resuspended with 0.5 mL of cell lysis buffer, and incubated at 30° C. for 5 min with shaking at 300 rpm. The cells were then recovered by centrifugation at 12,000 rpm for 1 min, and then resuspended and diluted with V mL of the 1×phi29 reaction buffer, followed by placing on ice.

4.2.4 Preparation of Microdroplet

The diameter of the microdroplet was controlled at about 20 μm. The generated microdroplets were collected on ice, and about 500 μL of microdroplets were collected.

4.2.5 iCSR Reaction

The collected microdroplets were aliquoted into PCR tubes at 30 μL/tube on ice. The recombinant phi29 DNA polymerases capable of reacting at a high temperature were tested and screened at the gradient temperatures in the PCR amplifier in this experiment, where the experimental conditions were set as 37° C.-55° C. for 2 h/16h, and then 85° C. for 15 min for thermal inactivating for the recombinant phi29 DNA polymerases.

4.2.6 Emulsion Breaking 4.2.6.1 The same number of PhaseLock tubes as the PCR tubes were centrifuged at 16,000 g for 30 s for a pretreatment.

4.2.6.2 Isopyknic PFO demulsifier was added to the the PCR tubes after the reaction of step 4.2.5, followed by transferring to a 1.5 mL EP tube after fully mixed and centrifuging at 14,000 rpm for 10 min. Then all the liquid was transferred into the phaseLock tubes and centrifuged at 16,000 g for 5 min. The upper liquid was transferred into new 8-strip PCR tubes.

4.2.7 Enzyme Digestion and Quantification with Qubit

9 μL of iCSR product was placed in the new 8-strip PCR tube and directly added with 0.5 μL of dpnI enzyme to digest the plasmid as the template and 0.5 μL of XbaI enzyme to cut the amplified product into single copies, followed by digesting at 37° C. for 2 h. Then, 1 μL of the digested product was taken to quantification with the Qubit dsDNA HS assay kit.

4.2.8 Second Amplification

A KAPA HiFi HotStart PCR Kit was used for amplification. The amount of reaction buffer should be adjusted as Mg$^{2+}$ had been accumulated in the previous steps in view of no purification steps involved, and a ready mix should not be used.

The reaction system was in a volume of 50 μL, including 8 μL of 5×HiFidelity buffer, 1.5 μL of 10 μM FW primer, 1.5 μL of 10 μM RE primer, 2 μL of template DNA taken from the tubes in step 3.7, 1.5 μL of 10 mM dNTP mix, 34.5 μL of NFH$_2$O and 1 μL of HiFi Enzyme.

Additionally, the vector taken as the template was amplified with ReadyMix as normal.

The reaction conditions were set as: (i) 95° C. for 3 min; (ii) 98° C. for 20 s, 65° C. for 15 s, 72° C. for 2 min, and (ii) was proformed for 35 cycles; and (iii) 72° C. for 10 min; and (iv) 4° C. for hold.

4.2.9 Recovery Via Gel

The PCR product added with 6×loading dye was subjected to agarose gel electrophoresis and was recovered after cutting the gel, according to the steps of the gel extraction kit. The recovered product was quantified.

4.2.10 In-Fusion Reaction

According to the instructions of the In-Fusion HD Cloning Kit, a recommended input amount is 50-100 ng when the insert length is 0.5-10 kb, and is 50-100 ng when the length of the vector is less than 10 kb. When there is only one insert, the recommended molar ratio of the insert and vector is 2:1. Accordingly, the reaction system in this Example was 10 µL, including 50 ng of purified PCR fragment, 78 ng of linearized vector, 2 µL of 5×In-fusion HD Enzyme mix and NFH₂O.

The reaction conditions were set as: (i) 50° C. for 15 min; and (ii) 4° C. for hold.

4.2.11 Transformation and Sequencing

The in-fusion product was directly transformed into KRX/BL21 competent cells (if a high transformation rate is required, the in-fusion product could be also transformed into DH5a cells first, and then transformed into BL21 cells after plasmid extraction), followed by transferring into LB liquid medium containing kanamycin directly. On the second day, the bacteria solution was prepared for expression inducing for the next round of screening. After the second round of screening, the bacteria on the plates were sequenced.

After the above steps, four recombinant phi29 DNA polymerases with combined mutations having higher activity were obtained, namely a recombinant phi29 DNA polymerase with T213K/L416A/V509E mutations, a recombinant phi29 DNA polymerase with M97T/Y224K/E515S mutations, a recombinant phi29 DNA polymerase with L123Q/T159A/Y347G mutations and a recombinant phi29 DNA polymerase with R96S/L123P/Y224K/L416A/E515S mutations.

The recombinant phi29 DNA polymerase with T213K/L416A/V509E mutations differs with the phi29 DNA polymerase shown in SEQ ID NO: 2 only in that T at position 213 of the latter was substituted by K, L at position 416 was substituted by A, and V at position 509 was substituted by E.

The recombinant phi29 DNA polymerase with M97T/Y224K/E515S mutations differs with the phi29 DNA polymerase shown in SEQ ID NO: 2 only in that M at position 97 of the latter was substituted by T, Y at position 224 was substituted by K, and E at position 515 was substituted by S.

The recombinant phi29 DNA polymerase with L123Q/T159A/Y347G mutations differs with the phi29 DNA polymerase shown in SEQ ID NO: 2 only in that L at position 123 of the latter was substituted by Q, T at position 159 was substituted by A, and Y at position 347 was substituted by G.

The recombinant phi29 DNA polymerase with R96S/L123P/Y224K/L416A/E515S mutations differs with the phi29 DNA polymerase shown in SEQ ID NO: 2 only in that R at position 96 of the latter was substituted by S, L at position 123 was substituted by P, Y at position 224 was substituted by K, L at position 416 was substituted by A, and E at position 515 was substituted by S.

4.3 Obtaintion of the recombinant phi29 DNA polymerase with combined mutations

The phi29 DNA polymerase shown in SEQ ID NO: 2, the recombinant phi29 DNA polymerase with T213K/L416A/V509E mutations, the recombinant phi29 DNA polymerase with M97T/Y224K/E515S mutations, the recombinant phi29 DNA polymerase with L123Q/T159A/Y347G mutations and the recombinant phi29 DNA polymerase with R96S/L123P/Y224K/L416A/E515S mutations were prepared.

4.4 Assay on Stability of the Phi29 DNA Polymerase with Combined Mutations

According to the method in Example 2, the recombinant phi29 DNA polymerase with T213K/L416A/V509E mutations, the recombinant phi29 DNA polymerase with M97T/Y224K/E515S mutations, the recombinant phi29 DNA polymerase with L123Q/T159A/Y347G mutations and the recombinant phi29 DNA polymerase with R96S/L123P/Y224K/L416A/E515S mutations were detected for the Tm values.

The detection results are shown in Table 8. The results show that three recombinant phi29 DNA polymerases with respective combined mutations were of a significantly increased Tm value as compared with the phi29 DNA polymerase shown in SEQ ID NO: 2, that is, the three recombinant phi29 DNA polymerases with respective combined mutations each exhibit a significantly improved stability.

TABLE 8

| | Tm(° C.) |
| --- | --- |
| phi29 DNA polymerase shown in SEQ ID NO: 2 | 48.5 |
| recombinant phi29 DNA polymerase with T213K/L416A/V509E mutations | 49.4 |
| recombinant phi29 DNA polymerase with M97T/Y224K/E515S mutations | 50.8 |
| recombinant phi29 DNA polymerase with L123Q/T159A/Y347G mutaions | 46.1 |
| recombinant phi29 DNA polymerase with R96S/L123P/Y224K/L416A/E515S mutations | 51.6 |

4.5 Assay on Specific Enzyme Activity of the Recombinant Phi29 DNA Polymerase with Combined Mutations According to the method in Example 3, the recombinant phi29 DNA polymerase with T213K/L416A/V509E mutations, the recombinant phi29 DNA polymerase with 5 M97T/Y224K/E515S mutations, the recombinant phi29 DNA polymerase with L123Q/T159A/Y347G mutations and the recombinant phi29 DNA polymerase with R96S/L123P/Y224K/L416A/E515S mutations were detected the specific enzyme activity.

The detection results are shown in Table 9. The results show that two recombinant phi29 DNA polymerases with respective combined mutations each were of a significantly increased specific enzyme activity as compared with the phi29 DNA polymerase shown in SEQ ID NO: 2, that is, the two recombinant phi29 DNA polymerases with respective combined mutations each exhibit a significantly improved specific enzyme activity.

TABLE 9

| | Specific enzyme activity (U/µg) |
| --- | --- |
| phi29 DNA polymerase shown in SEQ ID NO: 2 | 43 |
| recombinant phi29 DNA polymerase with T213K/L416A/V509E mutations | 52 |
| recombinant phi29 DNA polymerase with M97T/Y224K/E515S mutations | 55 |
| recombinant phi29 DNA polymerase with L123Q/T159A/Y347G mutations | 9 |
| recombinant phi29 DNA polymerase with R96S/L123P/Y224K/L416A/E515S mutations | 28 |

It can be seen that the recombinant phi29 DNA polymerase with T213K/L416A/V509E mutations and the recombinant phi29 DNA polymerase with M97T/Y224K/E515S mutations each have higher stability and specific enzyme activity, showing better effects. The recombinant phi29 DNA polymerase with R96S/L123P/Y224K/L416A/

E515S mutations has high stability but is slightly poor in specific enzyme activity. The recombinant phi29 DNA polymerase L123Q/T159A/Y347G mutations is poor in both stability and specific enzyme activity.

INDUSTRIAL APPLICATION

Compared with the existing phi29 DNA polymerase, 73 recombinant phi29 DNA polymerases with significantly improved stability and/or specific enzyme activity were prepared in embodiments of the present disclosure. These recombinant phi29 DNA polymerases not only have improved thermal stability, the polymerization activity and processivity are also improved. When the recombinant phi29 DNA polymerases prepared in embodiments of the present disclosure are used in amplification or sequencing, DNA can be efficiently and continuously synthesized, and the reaction efficiency is high. The present disclosure has important application value.

What is claimed is:

1. A protein of C1) or C2), wherein

C1) is a protein having DNA polymerase activity, consisting of the amino acid sequence of SEQ ID NO:2, wherein M position 97 relative to SEQ ID NO: 2 is substituted with P, Y or C;

C2) is a fusion protein obtained by attaching a tag to the N-terminus or/and C-terminus of the protein of C1).

2. The protein according to claim 1, wherein the protein has at higher stability or higher specific enzyme activity than that of a phi29 DNA polymerase comprising the amino acid sequence of SEQ ID NO: 2.

3. The protein according to claim 1, wherein the protein is any one of the following proteins:

protein a2, which is a protein consisting of the sequence of SEQ ID NO: 2, wherein M at position 97 is substituted with Y;

protein a40, which is a protein consisting of the sequence of SEQ ID NO: 2, wherein M at position 97 is substituted with C; and protein a41, which is a protein consisting of the sequence of SEQ ID NO: 2, wherein M at position 97 is substituted with P.

4. A nucleic acid molecule encoding a protein of C1) or C2), wherein

C1) is a protein having DNA polymerase activity, consisting of the amino acid sequence of SEQ ID NO:2, wherein M position 97 relative to SEQ ID NO: 2 is substituted with P, Y or C;

C2) is a fusion protein obtained by attaching a tag to the N-terminus or/and C-terminus of the protein of C1).

5. A DNA amplification method comprising contacting a DNA substrate with the protein of C1) or C2), wherein C1) is a protein having DNA polymerase activity, consisting of the amino acid sequence of SEQ ID NO:2, wherein M position 97 relative to SEQ ID NO: 2 is substituted with P, Y or C;

C2) is a fusion protein obtained by attaching a tag to the N-terminus or/and C-terminus of the protein of C1).

6. The DNA amplification method according to claim 5, wherein the amplification is second strand amplification, single cell amplification or plasmid amplification.

* * * * *

```
                            SEQUENCE LISTING

<160> NUMBER OF SEQ ID NOS: 158

<210> SEQ ID NO 1
<211> LENGTH: 1728
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1728)
<223> OTHER INFORMATION: CDS

<400> SEQUENCE: 1
atgaagcata tgccgcgcaa aatgtatagc tgcgactttg aaaccaccac caaagtggaa       60
gattgccgcg tttgggcgta tggctatatg aacatcgaag accacagcga atacaaaatt      120
ggcaacagcc tggatgaatt tatggcgtgg gtgctgaaag ttcaggcgga tctgtatttt      180
cacaacctga aatttgacgg cgcgttcatt attaactggc tggaacgcaa cggctttaaa      240
tggagcgcgc atggcttacc gaacacctat aacaccatta ttagccgcat gggccagtgg      300
tatatgattg atatctgcct gggctataaa ggcaaacgca agattcatac cgtgatctat      360
gatagcctga agaaactgcc gtttccggtg aaaaaaatcg cgaaggactt taaactgacc      420
gtgctgaaag gcgatattga ctaccataaa gaacgcccgg tgggctataa aattaccccg      480
gaggaatatg cgtacatcaa gaacgacatc cagattattg cggaagcgct gctgattcag      540
tttaaacagg gcctggatcg tatgaccgcg ggtagcgata gcctgaaagg ctttaaggac      600
attatcacca ccaagaagtt caagaaagtg tttccgaccc tgagcctggg cctggataaa      660
gaagtgcgct atgcgtatcg cggtggcttt acctggctga cgatcgctt taaggaaaag      720 gaaattggcg aaggcatggt gtttgatgtg aacagcctgt atccggcgca gatgtatagc      780
cgcctgctgc cgtatggtga accgattgtg tttgaaggca agtatgtgtg ggatgaagat      840
tatccgctgc acattcagca tattcgctgc gaattcgaac tgaaggaagg ctatattccg      900
accattcaga ttaaacgcag ccgctttat aaaggcaacg agtacctgaa aagcagcggc      960
ggcgaaattg cggatctgtg gctgagcaac gtggatctgg aactgatgaa agaacactac     1020
gatctgtaca acgtggaata tatcagcggc ctgaaattta aagcgaccac cggcctgttt     1080
aaggacttta tcgacaagtg gacctacatt aaaaccacca gcgaaggcgc gattaaacag     1140
ctggcgaaac tgatgctgaa cagcctgtat ggcaaatttg cgagcaaccc ggatgttacc     1200
ggcaaagtgc cgtatctgaa agaaaacggc gcgctgggct ttcgtttagg cgaagaggaa     1260
accaaagatc cggtgtatac cccgatgggc gtgtttatta ccgcgtgggc gcgctatacc     1320
accattaccg cggcgcaggc gtgttatgat cgcattatct attgcgatac cgatagcatt     1380
catctgaccg caccgaaat tccggatgtg atcaaagata ttgtggaccc gaaaaaactg     1440
ggctattggg cgcatgaaag cacctttaaa cgcgcgaaat atctgcgcca gaaaacctat     1500
```

-continued

--- atccaggaca tctacatgaa agaggtggat ggcaaactgg ttgaaggcag cccggatgat      1560
tataccgata ttaagttcag cgtgaaatgc gcgggcatga ccgataaaat taagaaggaa      1620
gtgaccttcg agaactttaa agtgggcttt agccgcaaaa tgaaaccgaa accggttcag      1680
gtgcctggcg tgttgttct ggtggatgat accttcacca tcaagtga                   1728

<210> SEQ ID NO 2
<211> LENGTH: 575
<212> TYPE: PRT
<213> ORGANISM: Artificial Sequence
<220> FEATURE:
<223> OTHER INFORMATION: Synthetic sequence

<400> SEQUENCE: 2

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
        130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met

```
                325               330               335
Lys Glu His Tyr Asp Leu Tyr Asn Val Glu Tyr Ile Ser Gly Leu Lys
            340               345               350

Phe Lys Ala Thr Thr Gly Leu Phe Lys Asp Phe Ile Asp Lys Trp Thr
            355               360               365

Tyr Ile Lys Thr Thr Ser Glu Gly Ala Ile Lys Gln Leu Ala Lys Leu
        370               375               380

Met Leu Asn Ser Leu Tyr Gly Lys Phe Ala Ser Asn Pro Asp Val Thr
    385               390               395               400

Gly Lys Val Pro Tyr Leu Lys Glu Asn Gly Ala Leu Gly Phe Arg Leu
                405               410               415

Gly Glu Glu Glu Thr Lys Asp Pro Val Tyr Thr Pro Met Gly Val Phe
            420               425               430

Ile Thr Ala Trp Ala Arg Tyr Thr Thr Ile Thr Ala Ala Gln Ala Cys
            435               440               445

Tyr Asp Arg Ile Ile Tyr Cys Asp Thr Asp Ser Ile His Leu Thr Gly
        450               455               460

Thr Glu Ile Pro Asp Val Ile Lys Asp Ile Val Asp Pro Lys Lys Leu
    465               470               475               480

Gly Tyr Trp Ala His Glu Ser Thr Phe Lys Arg Ala Lys Tyr Leu Arg
                485               490               495

Gln Lys Thr Tyr Ile Gln Asp Ile Tyr Met Lys Glu Val Asp Gly Lys
                500               505               510

Leu Val Glu Gly Ser Pro Asp Asp Tyr Thr Asp Ile Lys Phe Ser Val
            515               520               525

Lys Cys Ala Gly Met Thr Asp Lys Ile Lys Lys Glu Val Thr Phe Glu
        530               535               540

Asn Phe Lys Val Gly Phe Ser Arg Lys Met Lys Pro Lys Pro Val Gln
    545               550               555               560

Val Pro Gly Gly Val Val Leu Val Asp Asp Thr Phe Thr Ile Lys
                565               570               575
```

<210> SEQ ID NO 3
<211> LENGTH: 1788
<212> TYPE: DNA
<213> ORGANISM: Artificial Sequence
<220> FEATURE:
<223> OTHER INFORMATION: Synthetic sequence

<400> SEQUENCE: 3

```
atgggcagca gccatcatca tcatcatcac agcagcggcc tggtgccgcg cggcagccat      60
atgaagcata tgccgcgcaa aatgtatagc tgcgactttg aaaccaccac caaagtggaa     120
gattgccgcg tttgggcgta tggctatatg aacatcgaag accacagcga atacaaaatt     180
ggcaacagcc tggatgaatt tatggcgtgg gtgctgaaag ttcaggcgga tctgtatttt     240
cacaacctga aatttgacgg cgcgttcatt attaactggc tggaacgcaa cggctttaaa     300
tggagcgcgg atggcttacc gaacacctat aacaccatta ttagccgcat gggccagtgg     360
tatatgattg atatctgcct gggctataaa ggcaaacgca agattcatac cgtgatctat     420
gatagcctga agaaactgcc gtttccggtg aaaaaaatcg cgaaggactt taaactgacc     480
gtgctgaaag cgatattga ctaccataaa gaacgcccgg tgggctataa aattaccccg     540
gaggaatatg cgtacatcaa gaacgacatc cagattattg cggaagcgct gctgattcag     600
tttaaacagg gcctggatcg tatgaccgcg ggtagcgata gcctgaaagg ctttaaggac     660
```

-continued

```
attatcacca ccaagaagtt caagaaagtg tttccgaccc tgagcctggg cctggataaa      720
gaagtgcgct atgcgtatcg cggtggcttt acctggctga cgatcgcttt aaggaaaag       780 gaaattggcg aaggcatggt gtttgatgtg aacagcctgt atccggcgca gatgtatagc      840
cgcctgctgc cgtatggtga accgattgtg tttgaaggca gtatgtgtg gatgaagat       900 tatccgctgc acattcagca tattcgctgc gaattcgaac tgaaggaagg ctatattccg      960
accattcaga ttaaacgcag ccgctttat aaaggcaacg agtacctgaa aagcagcggc      1020
ggcgaaattg cggatctgtg gctgagcaac gtggatctgg aactgatgaa agaacactac     1080
gatctgtaca acgtgaata tatcagcggc ctgaaattta aagcgaccac cggcctgttt      1140
aaggacttta tcgacaagtg gacctacatt aaaaccacca gcgaaggcgc gattaaacag     1200
ctggcgaaac tgatgctgaa cagcctgtat ggcaaatttg cgagcaaccc ggatgttacc     1260
ggcaaagtgc cgtatctgaa agaaaacggc gcgctgggct ttcgtttagg cgaagaggaa     1320
accaaagatc cggtgtatac cccgatgggc gtgtttatta ccgcgtgggc cgctataccc     1380
accattaccg cggcgcaggc gtgttatgat cgcattatct attgcgatac cgatagcatt     1440
catctgaccg caccgaaat tccggatgtg atcaaagata ttgtggaccc gaaaaaactg     1500
ggctattggg cgcatgaaag cacctttaaa cgcgcgaaat atctgcgcca gaaaacctat     1560
atccaggaca tctacatgaa agaggtggat ggcaaactgg ttgaaggcag cccggatgat     1620
tataccgata ttaagttcag cgtgaaatgc gcgggcatga ccgataaaat taagaaggaa     1680
gtgaccttcg agaactttaa agtgggcttt agccgcaaaa tgaaaccgaa accggttcag     1740
gtgcctggcg tgttgttct ggtggatgat accttcacca tcaagtga               1788
```

```
<210> SEQ ID NO 4
<211> LENGTH: 595
<212> TYPE: PRT
<213> ORGANISM: Artificial Sequence
<220> FEATURE:
<223> OTHER INFORMATION: Synthetic sequence

<400> SEQUENCE: 4

Met Gly Ser Ser His His His His His His Ser Ser Gly Leu Val Pro
1               5                   10                  15

Arg Gly Ser His Met Lys His Met Pro Arg Lys Met Tyr Ser Cys Asp
            20                  25                  30

Phe Glu Thr Thr Thr Lys Val Glu Asp Cys Arg Val Trp Ala Tyr Gly
        35                  40                  45

Tyr Met Asn Ile Glu Asp His Ser Glu Tyr Lys Ile Gly Asn Ser Leu
    50                  55                  60

Asp Glu Phe Met Ala Trp Val Leu Lys Val Gln Ala Asp Leu Tyr Phe
65                  70                  75                  80

His Asn Leu Lys Phe Asp Gly Ala Phe Ile Ile Asn Trp Leu Glu Arg
                85                  90                  95

Asn Gly Phe Lys Trp Ser Ala Asp Gly Leu Pro Asn Thr Tyr Asn Thr
            100                 105                 110

Ile Ile Ser Arg Met Gly Gln Trp Tyr Met Ile Asp Ile Cys Leu Gly
        115                 120                 125

Tyr Lys Gly Lys Arg Lys Ile His Thr Val Ile Tyr Asp Ser Leu Lys
    130                 135                 140

Lys Leu Pro Phe Pro Val Lys Lys Ile Ala Lys Asp Phe Lys Leu Thr
145                 150                 155                 160

Val Leu Lys Gly Asp Ile Asp Tyr His Lys Glu Arg Pro Val Gly Tyr
```

-continued

```
                      165                 170                 175
Lys Ile Thr Pro Glu Glu Tyr Ala Tyr Ile Lys Asn Asp Ile Gln Ile
              180                 185                 190
Ile Ala Glu Ala Leu Leu Ile Gln Phe Lys Gln Gly Leu Asp Arg Met
              195                 200                 205
Thr Ala Gly Ser Asp Ser Leu Lys Gly Phe Lys Asp Ile Ile Thr Thr
              210                 215                 220
Lys Lys Phe Lys Lys Val Phe Pro Thr Leu Ser Leu Gly Leu Asp Lys
225                 230                 235                 240
Glu Val Arg Tyr Ala Tyr Arg Gly Gly Phe Thr Trp Leu Asn Asp Arg
                  245                 250                 255
Phe Lys Glu Lys Glu Ile Gly Glu Gly Met Val Phe Asp Val Asn Ser
              260                 265                 270
Leu Tyr Pro Ala Gln Met Tyr Ser Arg Leu Leu Pro Tyr Gly Glu Pro
              275                 280                 285
Ile Val Phe Glu Gly Lys Tyr Val Trp Asp Glu Asp Tyr Pro Leu His
              290                 295                 300
Ile Gln His Ile Arg Cys Glu Phe Glu Leu Lys Glu Gly Tyr Ile Pro
305                 310                 315                 320
Thr Ile Gln Ile Lys Arg Ser Arg Phe Tyr Lys Gly Asn Glu Tyr Leu
                  325                 330                 335
Lys Ser Ser Gly Gly Glu Ile Ala Asp Leu Trp Leu Ser Asn Val Asp
              340                 345                 350
Leu Glu Leu Met Lys Glu His Tyr Asp Leu Tyr Asn Val Glu Tyr Ile
              355                 360                 365
Ser Gly Leu Lys Phe Lys Ala Thr Thr Gly Leu Phe Lys Asp Phe Ile
              370                 375                 380
Asp Lys Trp Thr Tyr Ile Lys Thr Thr Ser Glu Gly Ala Ile Lys Gln
385                 390                 395                 400
Leu Ala Lys Leu Met Leu Asn Ser Leu Tyr Gly Lys Phe Ala Ser Asn
                  405                 410                 415
Pro Asp Val Thr Gly Lys Val Pro Tyr Leu Lys Glu Asn Gly Ala Leu
              420                 425                 430
Gly Phe Arg Leu Gly Glu Glu Glu Thr Lys Asp Pro Val Tyr Thr Pro
              435                 440                 445
Met Gly Val Phe Ile Thr Ala Trp Ala Arg Tyr Thr Thr Ile Thr Ala
              450                 455                 460
Ala Gln Ala Cys Tyr Asp Arg Ile Ile Tyr Cys Asp Thr Asp Ser Ile
465                 470                 475                 480
His Leu Thr Gly Thr Glu Ile Pro Asp Val Ile Lys Asp Ile Val Asp
                  485                 490                 495
Pro Lys Lys Leu Gly Tyr Trp Ala His Glu Ser Thr Phe Lys Arg Ala
              500                 505                 510
Lys Tyr Leu Arg Gln Lys Thr Tyr Ile Gln Asp Ile Tyr Met Lys Glu
              515                 520                 525
Val Asp Gly Lys Leu Val Glu Gly Ser Pro Asp Asp Tyr Thr Asp Ile
              530                 535                 540
Lys Phe Ser Val Lys Cys Ala Gly Met Thr Asp Lys Ile Lys Lys Glu
545                 550                 555                 560
Val Thr Phe Glu Asn Phe Lys Val Gly Phe Ser Arg Lys Met Lys Pro
                  565                 570                 575
Lys Pro Val Gln Val Pro Gly Gly Val Val Leu Val Asp Asp Thr Phe
              580                 585                 590
```

-continued

Thr Ile Lys
        595

<210> SEQ ID NO 5
<211> LENGTH: 33
<212> TYPE: DNA
<213> ORGANISM: Artificial Sequence
<220> FEATURE:
<223> OTHER INFORMATION: Synthetic sequence

<400> SEQUENCE: 5
gactttgaaa ccaccccgaa agtggaagat tgc                                    33

<210> SEQ ID NO 6
<211> LENGTH: 33
<212> TYPE: DNA
<213> ORGANISM: Artificial Sequence
<220> FEATURE:
<223> OTHER INFORMATION: Synthetic sequence

<400> SEQUENCE: 6
gcaatcttcc actttcgggg tggtttcaaa gtc                                    33

<210> SEQ ID NO 7
<211> LENGTH: 51
<212> TYPE: DNA
<213> ORGANISM: Artificial Sequence
<220> FEATURE:
<223> OTHER INFORMATION: Synthetic sequence

<400> SEQUENCE: 7
gatatcaatc atataccact ggccatagcg gctaataatg gtgttatagg t                51

<210> SEQ ID NO 8
<211> LENGTH: 51
<212> TYPE: DNA
<213> ORGANISM: Artificial Sequence
<220> FEATURE:
<223> OTHER INFORMATION: Synthetic sequence

<400> SEQUENCE: 8
acctataaca ccattattag ccgctatggc cagtggtata tgattgatat c                51

<210> SEQ ID NO 9
<211> LENGTH: 41
<212> TYPE: DNA
<213> ORGANISM: Artificial Sequence
<220> FEATURE:
<223> OTHER INFORMATION: Synthetic sequence

<400> SEQUENCE: 9
catataccac tggccgctgc ggctaataat ggtgttatag g                          41

<210> SEQ ID NO 10
<211> LENGTH: 41
<212> TYPE: DNA
<213> ORGANISM: Artificial Sequence
<220> FEATURE:
<223> OTHER INFORMATION: Synthetic sequence

<400> SEQUENCE: 10
cctataacac cattattagc cgcagcggcc agtggtatat g                          41

<210> SEQ ID NO 11
<211> LENGTH: 36

```
<212> TYPE: DNA
<213> ORGANISM: Artificial Sequence
<220> FEATURE:
<223> OTHER INFORMATION: Synthetic sequence

<400> SEQUENCE: 11
taccactggc ccctgcggct aataatggtg ttatag                              36

<210> SEQ ID NO 12
<211> LENGTH: 36
<212> TYPE: DNA
<213> ORGANISM: Artificial Sequence
<220> FEATURE:
<223> OTHER INFORMATION: Synthetic sequence

<400> SEQUENCE: 12
ctataacacc attattagcc gcaggggcca gtggta                              36

<210> SEQ ID NO 13
<211> LENGTH: 42
<212> TYPE: DNA
<213> ORGANISM: Artificial Sequence
<220> FEATURE:
<223> OTHER INFORMATION: Synthetic sequence

<400> SEQUENCE: 13
caatcatata ccactggccc tggcggctaa taatggtgtt at                       42

<210> SEQ ID NO 14
<211> LENGTH: 42
<212> TYPE: DNA
<213> ORGANISM: Artificial Sequence
<220> FEATURE:
<223> OTHER INFORMATION: Synthetic sequence

<400> SEQUENCE: 14
ataacaccat tattagccgc agggccagt ggtatatgat tg                        42

<210> SEQ ID NO 15
<211> LENGTH: 42
<212> TYPE: DNA
<213> ORGANISM: Artificial Sequence
<220> FEATURE:
<223> OTHER INFORMATION: Synthetic sequence

<400> SEQUENCE: 15
caatcatata ccactggccc ccgcggctaa taatggtgtt at                       42

<210> SEQ ID NO 16
<211> LENGTH: 42
<212> TYPE: DNA
<213> ORGANISM: Artificial Sequence
<220> FEATURE:
<223> OTHER INFORMATION: Synthetic sequence

<400> SEQUENCE: 16
ataacaccat tattagccgc gggggccagt ggtatatgat tg                       42

<210> SEQ ID NO 17
<211> LENGTH: 45
<212> TYPE: DNA
<213> ORGANISM: Artificial Sequence
<220> FEATURE:
<223> OTHER INFORMATION: Synthetic sequence

<400> SEQUENCE: 17
```

-continued

```
caccggaaac ggcagtttct tatagctatc atagatcacg gtatg                    45

<210> SEQ ID NO 18
<211> LENGTH: 45
<212> TYPE: DNA
<213> ORGANISM: Artificial Sequence
<220> FEATURE:
<223> OTHER INFORMATION: Synthetic sequence

<400> SEQUENCE: 18
cataccgtga tctatgatag ctataagaaa ctgccgtttc cggtg                    45

<210> SEQ ID NO 19
<211> LENGTH: 40
<212> TYPE: DNA
<213> ORGANISM: Artificial Sequence
<220> FEATURE:
<223> OTHER INFORMATION: Synthetic sequence

<400> SEQUENCE: 19
atatcgcctt tcagcacctt cagtttaaag tccttcgcga                          40

<210> SEQ ID NO 20
<211> LENGTH: 40
<212> TYPE: DNA
<213> ORGANISM: Artificial Sequence
<220> FEATURE:
<223> OTHER INFORMATION: Synthetic sequence

<400> SEQUENCE: 20
tcgcgaagga ctttaaactg aaggtgctga aaggcgatat                          40

<210> SEQ ID NO 21
<211> LENGTH: 40
<212> TYPE: DNA
<213> ORGANISM: Artificial Sequence
<220> FEATURE:
<223> OTHER INFORMATION: Synthetic sequence

<400> SEQUENCE: 21
aatatcgcct ttcagcacgt gcagtttaaa gtccttcgcg                          40

<210> SEQ ID NO 22
<211> LENGTH: 40
<212> TYPE: DNA
<213> ORGANISM: Artificial Sequence
<220> FEATURE:
<223> OTHER INFORMATION: Synthetic sequence

<400> SEQUENCE: 22
cgcgaaggac tttaaactgc acgtgctgaa aggcgatatt                          40

<210> SEQ ID NO 23
<211> LENGTH: 33
<212> TYPE: DNA
<213> ORGANISM: Artificial Sequence
<220> FEATURE:
<223> OTHER INFORMATION: Synthetic sequence

<400> SEQUENCE: 23
aaaggcgata ttgacccgca taaagaacgc ccg                                 33

<210> SEQ ID NO 24
<211> LENGTH: 33
<212> TYPE: DNA
<213> ORGANISM: Artificial Sequence
```

<220> FEATURE:
<223> OTHER INFORMATION: Synthetic sequence

<400> SEQUENCE: 24
cgggcgttct ttatgcgggt caatatcgcc ttt                                    33

<210> SEQ ID NO 25
<211> LENGTH: 33
<212> TYPE: DNA
<213> ORGANISM: Artificial Sequence
<220> FEATURE:
<223> OTHER INFORMATION: Synthetic sequence

<400> SEQUENCE: 25
aaaggcgata ttgacgaaca taaagaacgc ccg                                    33

<210> SEQ ID NO 26
<211> LENGTH: 33
<212> TYPE: DNA
<213> ORGANISM: Artificial Sequence
<220> FEATURE:
<223> OTHER INFORMATION: Synthetic sequence

<400> SEQUENCE: 26
cgggcgttct ttatgttcgt caatatcgcc ttt                                    33

<210> SEQ ID NO 27
<211> LENGTH: 33
<212> TYPE: DNA
<213> ORGANISM: Artificial Sequence
<220> FEATURE:
<223> OTHER INFORMATION: Synthetic sequence

<400> SEQUENCE: 27
ccggtgggct ataaaccgac cccggaggaa tat                                    33

<210> SEQ ID NO 28
<211> LENGTH: 33
<212> TYPE: DNA
<213> ORGANISM: Artificial Sequence
<220> FEATURE:
<223> OTHER INFORMATION: Synthetic sequence

<400> SEQUENCE: 28
atattcctcc ggggtcggtt tatagcccac cgg                                    33

<210> SEQ ID NO 29
<211> LENGTH: 33
<212> TYPE: DNA
<213> ORGANISM: Artificial Sequence
<220> FEATURE:
<223> OTHER INFORMATION: Synthetic sequence

<400> SEQUENCE: 29
gtgggctata aaattgcgcc ggaggaatat gcg                                    33

<210> SEQ ID NO 30
<211> LENGTH: 33
<212> TYPE: DNA
<213> ORGANISM: Artificial Sequence
<220> FEATURE:
<223> OTHER INFORMATION: Synthetic sequence

<400> SEQUENCE: 30
cgcatattcc tccggcgcaa ttttatagcc cac                                    33

```
<210> SEQ ID NO 31
<211> LENGTH: 54
<212> TYPE: DNA
<213> ORGANISM: Artificial Sequence
<220> FEATURE:
<223> OTHER INFORMATION: Synthetic sequence

<400> SEQUENCE: 31
gaaacacttt cttgaacttc ttggtctcga taatgtcctt aaagcctttc aggc          54

<210> SEQ ID NO 32
<211> LENGTH: 54
<212> TYPE: DNA
<213> ORGANISM: Artificial Sequence
<220> FEATURE:
<223> OTHER INFORMATION: Synthetic sequence

<400> SEQUENCE: 32
gcctgaaagg ctttaaggac attatcgaga ccaagaagtt caagaaagtg tttc          54

<210> SEQ ID NO 33
<211> LENGTH: 35
<212> TYPE: DNA
<213> ORGANISM: Artificial Sequence
<220> FEATURE:
<223> OTHER INFORMATION: Synthetic sequence

<400> SEQUENCE: 33
agccaccgcg atacgcctcg cgcacttctt tatcc                               35

<210> SEQ ID NO 34
<211> LENGTH: 35
<212> TYPE: DNA
<213> ORGANISM: Artificial Sequence
<220> FEATURE:
<223> OTHER INFORMATION: Synthetic sequence

<400> SEQUENCE: 34
ggataaagaa gtgcgcgagg cgtatcgcgg tggct                               35

<210> SEQ ID NO 35
<211> LENGTH: 33
<212> TYPE: DNA
<213> ORGANISM: Artificial Sequence
<220> FEATURE:
<223> OTHER INFORMATION: Synthetic sequence

<400> SEQUENCE: 35
attaaacgca gccgcagcta taaaggcaac gag                                 33

<210> SEQ ID NO 36
<211> LENGTH: 33
<212> TYPE: DNA
<213> ORGANISM: Artificial Sequence
<220> FEATURE:
<223> OTHER INFORMATION: Synthetic sequence

<400> SEQUENCE: 36
ctcgttgcct ttatagctgc ggctgcgttt aat                                 33

<210> SEQ ID NO 37
<211> LENGTH: 33
<212> TYPE: DNA
<213> ORGANISM: Artificial Sequence
<220> FEATURE:
<223> OTHER INFORMATION: Synthetic sequence
```

<400> SEQUENCE: 37
aaacgcagcc gctttaataa aggcaacgag tac                                     33

<210> SEQ ID NO 38
<211> LENGTH: 33
<212> TYPE: DNA
<213> ORGANISM: Artificial Sequence
<220> FEATURE:
<223> OTHER INFORMATION: Synthetic sequence

<400> SEQUENCE: 38
gtactcgttg cctttattaa agcggctgcg ttt                                     33

<210> SEQ ID NO 39
<211> LENGTH: 33
<212> TYPE: DNA
<213> ORGANISM: Artificial Sequence
<220> FEATURE:
<223> OTHER INFORMATION: Synthetic sequence

<400> SEQUENCE: 39
aaacgcagcc gctttggtaa aggcaacgag tac                                     33

<210> SEQ ID NO 40
<211> LENGTH: 33
<212> TYPE: DNA
<213> ORGANISM: Artificial Sequence
<220> FEATURE:
<223> OTHER INFORMATION: Synthetic sequence

<400> SEQUENCE: 40
gtactcgttg cctttaccaa agcggctgcg ttt                                     33

<210> SEQ ID NO 41
<211> LENGTH: 33
<212> TYPE: DNA
<213> ORGANISM: Artificial Sequence
<220> FEATURE:
<223> OTHER INFORMATION: Synthetic sequence

<400> SEQUENCE: 41
tacctgaaaa gcagccatgg cgaaattgcg gat                                     33

<210> SEQ ID NO 42
<211> LENGTH: 33
<212> TYPE: DNA
<213> ORGANISM: Artificial Sequence
<220> FEATURE:
<223> OTHER INFORMATION: Synthetic sequence

<400> SEQUENCE: 42
atccgcaatt tcgccatggc tgcttttcag gta                                     33

<210> SEQ ID NO 43
<211> LENGTH: 33
<212> TYPE: DNA
<213> ORGANISM: Artificial Sequence
<220> FEATURE:
<223> OTHER INFORMATION: Synthetic sequence

<400> SEQUENCE: 43
tacctgaaaa gcagcgaagg cgaaattgcg gat                                     33

<210> SEQ ID NO 44

-continued

```
<211> LENGTH: 33
<212> TYPE: DNA
<213> ORGANISM: Artificial Sequence
<220> FEATURE:
<223> OTHER INFORMATION: Synthetic sequence

<400> SEQUENCE: 44
atccgcaatt tcgccttcgc tgcttttcag gta                                33

<210> SEQ ID NO 45
<211> LENGTH: 33
<212> TYPE: DNA
<213> ORGANISM: Artificial Sequence
<220> FEATURE:
<223> OTHER INFORMATION: Synthetic sequence

<400> SEQUENCE: 45
tacctgaaaa gcagcgatgg cgaaattgcg gat                                33

<210> SEQ ID NO 46
<211> LENGTH: 33
<212> TYPE: DNA
<213> ORGANISM: Artificial Sequence
<220> FEATURE:
<223> OTHER INFORMATION: Synthetic sequence

<400> SEQUENCE: 46
atccgcaatt tcgccatcgc tgcttttcag gta                                33

<210> SEQ ID NO 47
<211> LENGTH: 33
<212> TYPE: DNA
<213> ORGANISM: Artificial Sequence
<220> FEATURE:
<223> OTHER INFORMATION: Synthetic sequence

<400> SEQUENCE: 47
tacctgaaaa gcagctgtgg cgaaattgcg gat                                33

<210> SEQ ID NO 48
<211> LENGTH: 33
<212> TYPE: DNA
<213> ORGANISM: Artificial Sequence
<220> FEATURE:
<223> OTHER INFORMATION: Synthetic sequence

<400> SEQUENCE: 48
atccgcaatt tcgccacagc tgcttttcag gta                                33

<210> SEQ ID NO 49
<211> LENGTH: 33
<212> TYPE: DNA
<213> ORGANISM: Artificial Sequence
<220> FEATURE:
<223> OTHER INFORMATION: Synthetic sequence

<400> SEQUENCE: 49
cactacgatc tgtaccgtgt ggaatatatc agc                                33

<210> SEQ ID NO 50
<211> LENGTH: 33
<212> TYPE: DNA
<213> ORGANISM: Artificial Sequence
<220> FEATURE:
<223> OTHER INFORMATION: Synthetic sequence

<400> SEQUENCE: 50
```

-continued

```
gctgatatat tccacacggt acagatcgta gtg                              33

<210> SEQ ID NO 51
<211> LENGTH: 33
<212> TYPE: DNA
<213> ORGANISM: Artificial Sequence
<220> FEATURE:
<223> OTHER INFORMATION: Synthetic sequence

<400> SEQUENCE: 51
tacgatctgt acaacgaaga atatatcagc ggc                              33

<210> SEQ ID NO 52
<211> LENGTH: 33
<212> TYPE: DNA
<213> ORGANISM: Artificial Sequence
<220> FEATURE:
<223> OTHER INFORMATION: Synthetic sequence

<400> SEQUENCE: 52
gccgctgata tattcttcgt tgtacagatc gta                              33

<210> SEQ ID NO 53
<211> LENGTH: 46
<212> TYPE: DNA
<213> ORGANISM: Artificial Sequence
<220> FEATURE:
<223> OTHER INFORMATION: Synthetic sequence

<400> SEQUENCE: 53
tttaaatttc aggccgctga taccttccac gttgtacaga tcgtag               46

<210> SEQ ID NO 54
<211> LENGTH: 46
<212> TYPE: DNA
<213> ORGANISM: Artificial Sequence
<220> FEATURE:
<223> OTHER INFORMATION: Synthetic sequence

<400> SEQUENCE: 54
ctacgatctg tacaacgtgg aaggtatcag cggcctgaaa tttaaa               46

<210> SEQ ID NO 55
<211> LENGTH: 33
<212> TYPE: DNA
<213> ORGANISM: Artificial Sequence
<220> FEATURE:
<223> OTHER INFORMATION: Synthetic sequence

<400> SEQUENCE: 55
atctacatga agaggaaga tggcaaactg gtt                              33

<210> SEQ ID NO 56
<211> LENGTH: 33
<212> TYPE: DNA
<213> ORGANISM: Artificial Sequence
<220> FEATURE:
<223> OTHER INFORMATION: Synthetic sequence

<400> SEQUENCE: 56
aaccagtttg ccatcttcct ctttcatgta gat                              33

<210> SEQ ID NO 57
<211> LENGTH: 41
<212> TYPE: DNA
```

-continued

```
<213> ORGANISM: Artificial Sequence
<220> FEATURE:
<223> OTHER INFORMATION: Synthetic sequence

<400> SEQUENCE: 57
catccgggct gccccaaacc agtttgccat ccacctcttt c                    41

<210> SEQ ID NO 58
<211> LENGTH: 41
<212> TYPE: DNA
<213> ORGANISM: Artificial Sequence
<220> FEATURE:
<223> OTHER INFORMATION: Synthetic sequence

<400> SEQUENCE: 58
gaaagaggtg gatggcaaac tggtttgggg cagcccggat g                    41

<210> SEQ ID NO 59
<211> LENGTH: 41
<212> TYPE: DNA
<213> ORGANISM: Artificial Sequence
<220> FEATURE:
<223> OTHER INFORMATION: Synthetic sequence

<400> SEQUENCE: 59
gaaagaggtg gatggcaaac tggttacggg cagcccggat g                    41

<210> SEQ ID NO 60
<211> LENGTH: 41
<212> TYPE: DNA
<213> ORGANISM: Artificial Sequence
<220> FEATURE:
<223> OTHER INFORMATION: Synthetic sequence

<400> SEQUENCE: 60
catccgggct gcccgtaacc agtttgccat ccacctcttt c                    41

<210> SEQ ID NO 61
<211> LENGTH: 34
<212> TYPE: DNA
<213> ORGANISM: Artificial Sequence
<220> FEATURE:
<223> OTHER INFORMATION: Synthetic sequence

<400> SEQUENCE: 61
gaggtggatg gcaaactggt ttcaggcagc ccgg                            34

<210> SEQ ID NO 62
<211> LENGTH: 34
<212> TYPE: DNA
<213> ORGANISM: Artificial Sequence
<220> FEATURE:
<223> OTHER INFORMATION: Synthetic sequence

<400> SEQUENCE: 62
ccgggctgcc tgaaaccagt ttgccatcca cctc                            34

<210> SEQ ID NO 63
<211> LENGTH: 34
<212> TYPE: DNA
<213> ORGANISM: Artificial Sequence
<220> FEATURE:
<223> OTHER INFORMATION: Synthetic sequence

<400> SEQUENCE: 63
ccgggctgcc tctaaccagt ttgccatcca cctc                            34
```

-continued

```
<210> SEQ ID NO 64
<211> LENGTH: 34
<212> TYPE: DNA
<213> ORGANISM: Artificial Sequence
<220> FEATURE:
<223> OTHER INFORMATION: Synthetic sequence

<400> SEQUENCE: 64
gaggtggatg gcaaactggt tagaggcagc ccgg                                        34

<210> SEQ ID NO 65
<211> LENGTH: 32
<212> TYPE: DNA
<213> ORGANISM: Artificial Sequence
<220> FEATURE:
<223> OTHER INFORMATION: Synthetic sequence

<400> SEQUENCE: 65
ccgggctgcc attaaccagt ttgccatcca cc                                          32

<210> SEQ ID NO 66
<211> LENGTH: 32
<212> TYPE: DNA
<213> ORGANISM: Artificial Sequence
<220> FEATURE:
<223> OTHER INFORMATION: Synthetic sequence

<400> SEQUENCE: 66
ggtggatggc aaactggtta atggcagccc gg                                          32

<210> SEQ ID NO 67
<211> LENGTH: 34
<212> TYPE: DNA
<213> ORGANISM: Artificial Sequence
<220> FEATURE:
<223> OTHER INFORMATION: Synthetic sequence

<400> SEQUENCE: 67
ccgggctgcc tataaccagt ttgccatcca cctc                                        34

<210> SEQ ID NO 68
<211> LENGTH: 34
<212> TYPE: DNA
<213> ORGANISM: Artificial Sequence
<220> FEATURE:
<223> OTHER INFORMATION: Synthetic sequence

<400> SEQUENCE: 68
gaggtggatg gcaaactggt tataggcagc ccgg                                        34

<210> SEQ ID NO 69
<211> LENGTH: 41
<212> TYPE: DNA
<213> ORGANISM: Artificial Sequence
<220> FEATURE:
<223> OTHER INFORMATION: Synthetic sequence

<400> SEQUENCE: 69
catccgggct gccgaaaacc agtttgccat ccacctcttt c                                41

<210> SEQ ID NO 70
<211> LENGTH: 41
<212> TYPE: DNA
<213> ORGANISM: Artificial Sequence
<220> FEATURE:
```

-continued

<223> OTHER INFORMATION: Synthetic sequence

<400> SEQUENCE: 70
gaaagaggtg gatggcaaac tggttttcgg cagcccggat g                          41

<210> SEQ ID NO 71
<211> LENGTH: 47
<212> TYPE: DNA
<213> ORGANISM: Artificial Sequence
<220> FEATURE:
<223> OTHER INFORMATION: Synthetic sequence

<400> SEQUENCE: 71
catataccac tggcccatct cgctaataat ggtgttatag gtgttcg                    47

<210> SEQ ID NO 72
<211> LENGTH: 47
<212> TYPE: DNA
<213> ORGANISM: Artificial Sequence
<220> FEATURE:
<223> OTHER INFORMATION: Synthetic sequence

<400> SEQUENCE: 72
cgaacaccta taacaccatt attagcgaga tgggccagtg gtatatg                    47

<210> SEQ ID NO 73
<211> LENGTH: 33
<212> TYPE: DNA
<213> ORGANISM: Artificial Sequence
<220> FEATURE:
<223> OTHER INFORMATION: Synthetic sequence

<400> SEQUENCE: 73
aacaccatta ttagcaatat gggccagtgg tat                                   33

<210> SEQ ID NO 74
<211> LENGTH: 33
<212> TYPE: DNA
<213> ORGANISM: Artificial Sequence
<220> FEATURE:
<223> OTHER INFORMATION: Synthetic sequence

<400> SEQUENCE: 74
ataccactgg cccatattgc taataatggt gtt                                   33

<210> SEQ ID NO 75
<211> LENGTH: 33
<212> TYPE: DNA
<213> ORGANISM: Artificial Sequence
<220> FEATURE:
<223> OTHER INFORMATION: Synthetic sequence

<400> SEQUENCE: 75
aacaccatta ttagcgcgat gggccagtgg tat                                   33

<210> SEQ ID NO 76
<211> LENGTH: 33
<212> TYPE: DNA
<213> ORGANISM: Artificial Sequence
<220> FEATURE:
<223> OTHER INFORMATION: Synthetic sequence

<400> SEQUENCE: 76
ataccactgg cccatcgcgc taataatggt gtt                                   33

```
<210> SEQ ID NO 77
<211> LENGTH: 33
<212> TYPE: DNA
<213> ORGANISM: Artificial Sequence
<220> FEATURE:
<223> OTHER INFORMATION: Synthetic sequence

<400> SEQUENCE: 77
aacaccatta ttagcggtat gggccagtgg tat                               33

<210> SEQ ID NO 78
<211> LENGTH: 33
<212> TYPE: DNA
<213> ORGANISM: Artificial Sequence
<220> FEATURE:
<223> OTHER INFORMATION: Synthetic sequence

<400> SEQUENCE: 78
ataccactgg cccataccgc taataatggt gtt                               33

<210> SEQ ID NO 79
<211> LENGTH: 47
<212> TYPE: DNA
<213> ORGANISM: Artificial Sequence
<220> FEATURE:
<223> OTHER INFORMATION: Synthetic sequence

<400> SEQUENCE: 79
catataccac tggcccatct tgctaataat ggtgttatag gtgttcg               47

<210> SEQ ID NO 80
<211> LENGTH: 47
<212> TYPE: DNA
<213> ORGANISM: Artificial Sequence
<220> FEATURE:
<223> OTHER INFORMATION: Synthetic sequence

<400> SEQUENCE: 80
cgaacaccta taacaccatt attagcaaga tgggccagtg gtatatg               47

<210> SEQ ID NO 81
<211> LENGTH: 35
<212> TYPE: DNA
<213> ORGANISM: Artificial Sequence
<220> FEATURE:
<223> OTHER INFORMATION: Synthetic sequence

<400> SEQUENCE: 81
catataccac tggcccacgc ggctaataat ggtgt                            35

<210> SEQ ID NO 82
<211> LENGTH: 35
<212> TYPE: DNA
<213> ORGANISM: Artificial Sequence
<220> FEATURE:
<223> OTHER INFORMATION: Synthetic sequence

<400> SEQUENCE: 82
acaccattat tagccgcgtg ggccagtggt atatg                            35

<210> SEQ ID NO 83
<211> LENGTH: 49
<212> TYPE: DNA
<213> ORGANISM: Artificial Sequence
<220> FEATURE:
<223> OTHER INFORMATION: Synthetic sequence
```

<400> SEQUENCE: 83
atatcaatca tataccactg gccgcagcgg ctaataatgg tgttatagg                                    49

<210> SEQ ID NO 84
<211> LENGTH: 49
<212> TYPE: DNA
<213> ORGANISM: Artificial Sequence
<220> FEATURE:
<223> OTHER INFORMATION: Synthetic sequence

<400> SEQUENCE: 84
cctataacac cattattagc cgctgcggcc agtggtatat gattgatat                                    49

<210> SEQ ID NO 85
<211> LENGTH: 42
<212> TYPE: DNA
<213> ORGANISM: Artificial Sequence
<220> FEATURE:
<223> OTHER INFORMATION: Synthetic sequence

<400> SEQUENCE: 85
ataacaccat tattagccgc ccgggccagt ggtatatgat tg                                           42

<210> SEQ ID NO 86
<211> LENGTH: 42
<212> TYPE: DNA
<213> ORGANISM: Artificial Sequence
<220> FEATURE:
<223> OTHER INFORMATION: Synthetic sequence

<400> SEQUENCE: 86
caatcatata ccactggccc gggcggctaa taatggtgtt at                                           42

<210> SEQ ID NO 87
<211> LENGTH: 42
<212> TYPE: DNA
<213> ORGANISM: Artificial Sequence
<220> FEATURE:
<223> OTHER INFORMATION: Synthetic sequence

<400> SEQUENCE: 87
caatcatata ccactggccc cagcggctaa taatggtgtt at                                           42

<210> SEQ ID NO 88
<211> LENGTH: 42
<212> TYPE: DNA
<213> ORGANISM: Artificial Sequence
<220> FEATURE:
<223> OTHER INFORMATION: Synthetic sequence

<400> SEQUENCE: 88
ataacaccat tattagccgc tggggccagt ggtatatgat tg                                           42

<210> SEQ ID NO 89
<211> LENGTH: 41
<212> TYPE: DNA
<213> ORGANISM: Artificial Sequence
<220> FEATURE:
<223> OTHER INFORMATION: Synthetic sequence

<400> SEQUENCE: 89
catataccac tggccattgc ggctaataat ggtgttatag g                                            41

<210> SEQ ID NO 90
<211> LENGTH: 41

```
<212> TYPE: DNA
<213> ORGANISM: Artificial Sequence
<220> FEATURE:
<223> OTHER INFORMATION: Synthetic sequence

<400> SEQUENCE: 90
cctataacac cattattagc cgcaatggcc agtggtatat g                      41

<210> SEQ ID NO 91
<211> LENGTH: 51
<212> TYPE: DNA
<213> ORGANISM: Artificial Sequence
<220> FEATURE:
<223> OTHER INFORMATION: Synthetic sequence

<400> SEQUENCE: 91
gatatcaatc atataccact ggccatcgcg gctaataatg gtgttatagg t           51

<210> SEQ ID NO 92
<211> LENGTH: 51
<212> TYPE: DNA
<213> ORGANISM: Artificial Sequence
<220> FEATURE:
<223> OTHER INFORMATION: Synthetic sequence

<400> SEQUENCE: 92
acctataaca ccattattag ccgcgatggc cagtggtata tgattgatat c           51

<210> SEQ ID NO 93
<211> LENGTH: 42
<212> TYPE: DNA
<213> ORGANISM: Artificial Sequence
<220> FEATURE:
<223> OTHER INFORMATION: Synthetic sequence

<400> SEQUENCE: 93
caatcatata ccactggccc tcgcggctaa taatggtgtt at                     42

<210> SEQ ID NO 94
<211> LENGTH: 42
<212> TYPE: DNA
<213> ORGANISM: Artificial Sequence
<220> FEATURE:
<223> OTHER INFORMATION: Synthetic sequence

<400> SEQUENCE: 94
ataacaccat tattagccgc gagggccagt ggtatatgat tg                     42

<210> SEQ ID NO 95
<211> LENGTH: 51
<212> TYPE: DNA
<213> ORGANISM: Artificial Sequence
<220> FEATURE:
<223> OTHER INFORMATION: Synthetic sequence

<400> SEQUENCE: 95
gatatcaatc atataccact ggccatagcg gctaataatg gtgttatagg t           51

<210> SEQ ID NO 96
<211> LENGTH: 51
<212> TYPE: DNA
<213> ORGANISM: Artificial Sequence
<220> FEATURE:
<223> OTHER INFORMATION: Synthetic sequence

<400> SEQUENCE: 96
```
acctataaca ccattattag ccgctatggc cagtggtata tgattgatat c                                51

<210> SEQ ID NO 97
<211> LENGTH: 36
<212> TYPE: DNA
<213> ORGANISM: Artificial Sequence
<220> FEATURE:
<223> OTHER INFORMATION: Synthetic sequence

<400> SEQUENCE: 97
taccactggc ccctgcggct aataatggtg ttatag                                                  36

<210> SEQ ID NO 98
<211> LENGTH: 36
<212> TYPE: DNA
<213> ORGANISM: Artificial Sequence
<220> FEATURE:
<223> OTHER INFORMATION: Synthetic sequence

<400> SEQUENCE: 98
ctataacacc attattagcc gcagggggcca gtggta                                                 36

<210> SEQ ID NO 99
<211> LENGTH: 41
<212> TYPE: DNA
<213> ORGANISM: Artificial Sequence
<220> FEATURE:
<223> OTHER INFORMATION: Synthetic sequence

<400> SEQUENCE: 99
catataccac tggccgctgc ggctaataat ggtgttatag g                                            41

<210> SEQ ID NO 100
<211> LENGTH: 41
<212> TYPE: DNA
<213> ORGANISM: Artificial Sequence
<220> FEATURE:
<223> OTHER INFORMATION: Synthetic sequence

<400> SEQUENCE: 100
cctataacac cattattagc cgcagcggcc agtggtatat g                                            41

<210> SEQ ID NO 101
<211> LENGTH: 43
<212> TYPE: DNA
<213> ORGANISM: Artificial Sequence
<220> FEATURE:
<223> OTHER INFORMATION: Synthetic sequence

<400> SEQUENCE: 101
cagatatcaa tcatatacca cacgcccatg cggctaataa tgg                                          43

<210> SEQ ID NO 102
<211> LENGTH: 43
<212> TYPE: DNA
<213> ORGANISM: Artificial Sequence
<220> FEATURE:
<223> OTHER INFORMATION: Synthetic sequence

<400> SEQUENCE: 102
ccattattag ccgcatgggc gtgtggtata tgattgatat ctg                                          43

<210> SEQ ID NO 103
<211> LENGTH: 40
<212> TYPE: DNA
<213> ORGANISM: Artificial Sequence -continued

```
<220> FEATURE:
<223> OTHER INFORMATION: Synthetic sequence

<400> SEQUENCE: 103
gatatcaatc atataccact cgcccatgcg gctaataatg                              40

<210> SEQ ID NO 104
<211> LENGTH: 40
<212> TYPE: DNA
<213> ORGANISM: Artificial Sequence
<220> FEATURE:
<223> OTHER INFORMATION: Synthetic sequence

<400> SEQUENCE: 104
cattattagc cgcatgggcg agtggtatat gattgatatc                              40

<210> SEQ ID NO 105
<211> LENGTH: 33
<212> TYPE: DNA
<213> ORGANISM: Artificial Sequence
<220> FEATURE:
<223> OTHER INFORMATION: Synthetic sequence

<400> SEQUENCE: 105
attagccgca tgggcacctg gtatatgatt gat                                     33

<210> SEQ ID NO 106
<211> LENGTH: 33
<212> TYPE: DNA
<213> ORGANISM: Artificial Sequence
<220> FEATURE:
<223> OTHER INFORMATION: Synthetic sequence

<400> SEQUENCE: 106
atcaatcata taccaggtgc ccatgcggct aat                                     33

<210> SEQ ID NO 107
<211> LENGTH: 40
<212> TYPE: DNA
<213> ORGANISM: Artificial Sequence
<220> FEATURE:
<223> OTHER INFORMATION: Synthetic sequence

<400> SEQUENCE: 107
cggaaacggc agtttcttcg cgctatcata gatcacggta                              40

<210> SEQ ID NO 108
<211> LENGTH: 40
<212> TYPE: DNA
<213> ORGANISM: Artificial Sequence
<220> FEATURE:
<223> OTHER INFORMATION: Synthetic sequence

<400> SEQUENCE: 108
taccgtgatc tatgatagcg cgaagaaact gccgtttccg                              40

<210> SEQ ID NO 109
<211> LENGTH: 45
<212> TYPE: DNA
<213> ORGANISM: Artificial Sequence
<220> FEATURE:
<223> OTHER INFORMATION: Synthetic sequence

<400> SEQUENCE: 109
caccggaaac ggcagtttct tgcagctatc atagatcacg gtatg                        45
```

-continued

```
<210> SEQ ID NO 110
<211> LENGTH: 45
<212> TYPE: DNA
<213> ORGANISM: Artificial Sequence
<220> FEATURE:
<223> OTHER INFORMATION: Synthetic sequence

<400> SEQUENCE: 110
cataccgtga tctatgatag ctgcaagaaa ctgccgtttc cggtg                          45

<210> SEQ ID NO 111
<211> LENGTH: 35
<212> TYPE: DNA
<213> ORGANISM: Artificial Sequence
<220> FEATURE:
<223> OTHER INFORMATION: Synthetic sequence

<400> SEQUENCE: 111
gaaacggcag tttcttctgg ctatcataga tcacg                                     35

<210> SEQ ID NO 112
<211> LENGTH: 35
<212> TYPE: DNA
<213> ORGANISM: Artificial Sequence
<220> FEATURE:
<223> OTHER INFORMATION: Synthetic sequence

<400> SEQUENCE: 112
cgtgatctat gatagccaga agaaactgcc gtttc                                     35

<210> SEQ ID NO 113
<211> LENGTH: 37
<212> TYPE: DNA
<213> ORGANISM: Artificial Sequence
<220> FEATURE:
<223> OTHER INFORMATION: Synthetic sequence

<400> SEQUENCE: 113
gaaacggcag tttcttcatg ctatcataga tcacggt                                   37

<210> SEQ ID NO 114
<211> LENGTH: 37
<212> TYPE: DNA
<213> ORGANISM: Artificial Sequence
<220> FEATURE:
<223> OTHER INFORMATION: Synthetic sequence

<400> SEQUENCE: 114
accgtgatct atgatagcat gaagaaactg ccgtttc                                   37

<210> SEQ ID NO 115
<211> LENGTH: 45
<212> TYPE: DNA
<213> ORGANISM: Artificial Sequence
<220> FEATURE:
<223> OTHER INFORMATION: Synthetic sequence

<400> SEQUENCE: 115
caccggaaac ggcagtttct tattgctatc atagatcacg gtatg                          45

<210> SEQ ID NO 116
<211> LENGTH: 45
<212> TYPE: DNA
<213> ORGANISM: Artificial Sequence
<220> FEATURE:
<223> OTHER INFORMATION: Synthetic sequence
```

<400> SEQUENCE: 116
cataccgtga tctatgatag caataagaaa ctgccgtttc cggtg                          45

<210> SEQ ID NO 117
<211> LENGTH: 35
<212> TYPE: DNA
<213> ORGANISM: Artificial Sequence
<220> FEATURE:
<223> OTHER INFORMATION: Synthetic sequence

<400> SEQUENCE: 117
acatcaagaa cgacatcgag attattgcgg aagcg                                     35

<210> SEQ ID NO 118
<211> LENGTH: 35
<212> TYPE: DNA
<213> ORGANISM: Artificial Sequence
<220> FEATURE:
<223> OTHER INFORMATION: Synthetic sequence

<400> SEQUENCE: 118
cgcttccgca ataatctcga tgtcgttctt gatgt                                     35

<210> SEQ ID NO 119
<211> LENGTH: 33
<212> TYPE: DNA
<213> ORGANISM: Artificial Sequence
<220> FEATURE:
<223> OTHER INFORMATION: Synthetic sequence

<400> SEQUENCE: 119
atcaagaacg acatcaaaat tattgcggaa gcg                                       33

<210> SEQ ID NO 120
<211> LENGTH: 33
<212> TYPE: DNA
<213> ORGANISM: Artificial Sequence
<220> FEATURE:
<223> OTHER INFORMATION: Synthetic sequence

<400> SEQUENCE: 120
cgcttccgca ataattttga tgtcgttctt gat                                       33

<210> SEQ ID NO 121
<211> LENGTH: 33
<212> TYPE: DNA
<213> ORGANISM: Artificial Sequence
<220> FEATURE:
<223> OTHER INFORMATION: Synthetic sequence

<400> SEQUENCE: 121
aaggacatta tcaccaagaa gaagttcaag aaa                                       33

<210> SEQ ID NO 122
<211> LENGTH: 33
<212> TYPE: DNA
<213> ORGANISM: Artificial Sequence
<220> FEATURE:
<223> OTHER INFORMATION: Synthetic sequence

<400> SEQUENCE: 122
tttcttgaac ttcttcttgg tgataatgtc ctt                                       33

<210> SEQ ID NO 123

```
<211> LENGTH: 33
<212> TYPE: DNA
<213> ORGANISM: Artificial Sequence
<220> FEATURE:
<223> OTHER INFORMATION: Synthetic sequence

<400> SEQUENCE: 123
aagaaagtgt ttccgaaact gagcctgggc ctg                                    33

<210> SEQ ID NO 124
<211> LENGTH: 33
<212> TYPE: DNA
<213> ORGANISM: Artificial Sequence
<220> FEATURE:
<223> OTHER INFORMATION: Synthetic sequence

<400> SEQUENCE: 124
caggcccagg ctcagtttcg gaaacacttt ctt                                    33

<210> SEQ ID NO 125
<211> LENGTH: 33
<212> TYPE: DNA
<213> ORGANISM: Artificial Sequence
<220> FEATURE:
<223> OTHER INFORMATION: Synthetic sequence

<400> SEQUENCE: 125
ccgaccctga gcctgaaact ggataaagaa gtg                                    33

<210> SEQ ID NO 126
<211> LENGTH: 33
<212> TYPE: DNA
<213> ORGANISM: Artificial Sequence
<220> FEATURE:
<223> OTHER INFORMATION: Synthetic sequence

<400> SEQUENCE: 126
cacttcttta tccagtttca ggctcagggt cgg                                    33

<210> SEQ ID NO 127
<211> LENGTH: 43
<212> TYPE: DNA
<213> ORGANISM: Artificial Sequence
<220> FEATURE:
<223> OTHER INFORMATION: Synthetic sequence

<400> SEQUENCE: 127
ggatacaggc tgtttatatc aaacaccatg ccttcgccaa ttt                         43

<210> SEQ ID NO 128
<211> LENGTH: 43
<212> TYPE: DNA
<213> ORGANISM: Artificial Sequence
<220> FEATURE:
<223> OTHER INFORMATION: Synthetic sequence

<400> SEQUENCE: 128
aaattggcga aggcatggtg tttgatataa acagcctgta tcc                         43

<210> SEQ ID NO 129
<211> LENGTH: 33
<212> TYPE: DNA
<213> ORGANISM: Artificial Sequence
<220> FEATURE:
<223> OTHER INFORMATION: Synthetic sequence

<400> SEQUENCE: 129
```

-continued

---

```
tatggtgaac cgattcgttt tgaaggcaag tat                                      33

<210> SEQ ID NO 130
<211> LENGTH: 33
<212> TYPE: DNA
<213> ORGANISM: Artificial Sequence
<220> FEATURE:
<223> OTHER INFORMATION: Synthetic sequence

<400> SEQUENCE: 130
atacttgcct tcaaaacgaa tcggttcacc ata                                      33

<210> SEQ ID NO 131
<211> LENGTH: 33
<212> TYPE: DNA
<213> ORGANISM: Artificial Sequence
<220> FEATURE:
<223> OTHER INFORMATION: Synthetic sequence

<400> SEQUENCE: 131
cactacgatc tgtacaaagt ggaatatatc agc                                      33

<210> SEQ ID NO 132
<211> LENGTH: 33
<212> TYPE: DNA
<213> ORGANISM: Artificial Sequence
<220> FEATURE:
<223> OTHER INFORMATION: Synthetic sequence

<400> SEQUENCE: 132
gctgatatat tccactttgt acagatcgta gtg                                      33

<210> SEQ ID NO 133
<211> LENGTH: 33
<212> TYPE: DNA
<213> ORGANISM: Artificial Sequence
<220> FEATURE:
<223> OTHER INFORMATION: Synthetic sequence

<400> SEQUENCE: 133
atcgacaagt ggaccgatat taaaaccacc agc                                      33

<210> SEQ ID NO 134
<211> LENGTH: 33
<212> TYPE: DNA
<213> ORGANISM: Artificial Sequence
<220> FEATURE:
<223> OTHER INFORMATION: Synthetic sequence

<400> SEQUENCE: 134
gctggtggtt ttaatatcgg tccacttgtc gat                                      33

<210> SEQ ID NO 135
<211> LENGTH: 33
<212> TYPE: DNA
<213> ORGANISM: Artificial Sequence
<220> FEATURE:
<223> OTHER INFORMATION: Synthetic sequence

<400> SEQUENCE: 135
atcgacaagt ggaccaatat taaaaccacc agc                                      33

<210> SEQ ID NO 136
<211> LENGTH: 33
<212> TYPE: DNA
```

<213> ORGANISM: Artificial Sequence
<220> FEATURE:
<223> OTHER INFORMATION: Synthetic sequence

<400> SEQUENCE: 136
gctggtggtt ttaatattgg tccacttgtc gat                                    33

<210> SEQ ID NO 137
<211> LENGTH: 36
<212> TYPE: DNA
<213> ORGANISM: Artificial Sequence
<220> FEATURE:
<223> OTHER INFORMATION: Synthetic sequence

<400> SEQUENCE: 137
ctttcagata cggcactaag ccggtaacat ccgggt                                 36

<210> SEQ ID NO 138
<211> LENGTH: 36
<212> TYPE: DNA
<213> ORGANISM: Artificial Sequence
<220> FEATURE:
<223> OTHER INFORMATION: Synthetic sequence

<400> SEQUENCE: 138
acccggatgt taccggctta gtgccgtatc tgaaag                                 36

<210> SEQ ID NO 139
<211> LENGTH: 33
<212> TYPE: DNA
<213> ORGANISM: Artificial Sequence
<220> FEATURE:
<223> OTHER INFORMATION: Synthetic sequence

<400> SEQUENCE: 139
gcgctgggct ttcgtgcggg cgaagaggaa acc                                    33

<210> SEQ ID NO 140
<211> LENGTH: 33
<212> TYPE: DNA
<213> ORGANISM: Artificial Sequence
<220> FEATURE:
<223> OTHER INFORMATION: Synthetic sequence

<400> SEQUENCE: 140
ggtttcctct tcgcccgcac gaaagcccag cgc                                    33

<210> SEQ ID NO 141
<211> LENGTH: 41
<212> TYPE: DNA
<213> ORGANISM: Artificial Sequence
<220> FEATURE:
<223> OTHER INFORMATION: Synthetic sequence

<400> SEQUENCE: 141
catccgggct gccgaaaacc agtttgccat ccacctcttt c                           41

<210> SEQ ID NO 142
<211> LENGTH: 41
<212> TYPE: DNA
<213> ORGANISM: Artificial Sequence
<220> FEATURE:
<223> OTHER INFORMATION: Synthetic sequence

<400> SEQUENCE: 142
gaaagaggtg gatggcaaac tggttttcgg cagcccggat g                           41

```
<210> SEQ ID NO 143
<211> LENGTH: 32
<212> TYPE: DNA
<213> ORGANISM: Artificial Sequence
<220> FEATURE:
<223> OTHER INFORMATION: Synthetic sequence

<400> SEQUENCE: 143
ccgggctgcc atgaaccagt ttgccatcca cc                                      32

<210> SEQ ID NO 144
<211> LENGTH: 32
<212> TYPE: DNA
<213> ORGANISM: Artificial Sequence
<220> FEATURE:
<223> OTHER INFORMATION: Synthetic sequence

<400> SEQUENCE: 144
ggtggatggc aaactggttc atggcagccc gg                                      32

<210> SEQ ID NO 145
<211> LENGTH: 32
<212> TYPE: DNA
<213> ORGANISM: Artificial Sequence
<220> FEATURE:
<223> OTHER INFORMATION: Synthetic sequence

<400> SEQUENCE: 145
ccgggctgcc ctgaaccagt ttgccatcca cc                                      32

<210> SEQ ID NO 146
<211> LENGTH: 32
<212> TYPE: DNA
<213> ORGANISM: Artificial Sequence
<220> FEATURE:
<223> OTHER INFORMATION: Synthetic sequence

<400> SEQUENCE: 146
ggtggatggc aaactggttc agggcagccc gg                                      32

<210> SEQ ID NO 147
<211> LENGTH: 41
<212> TYPE: DNA
<213> ORGANISM: Artificial Sequence
<220> FEATURE:
<223> OTHER INFORMATION: Synthetic sequence

<400> SEQUENCE: 147
gaaagaggtg gatggcaaac tggttacggg cagcccggat g                            41

<210> SEQ ID NO 148
<211> LENGTH: 41
<212> TYPE: DNA
<213> ORGANISM: Artificial Sequence
<220> FEATURE:
<223> OTHER INFORMATION: Synthetic sequence

<400> SEQUENCE: 148
catccgggct gcccgtaacc agtttgccat ccacctcttt c                            41

<210> SEQ ID NO 149
<211> LENGTH: 33
<212> TYPE: DNA
<213> ORGANISM: Artificial Sequence
<220> FEATURE:
```

<223> OTHER INFORMATION: Synthetic sequence

<400> SEQUENCE: 149
gatgattata ccgatgtgaa gttcagcgtg aaa                                          33

<210> SEQ ID NO 150
<211> LENGTH: 33
<212> TYPE: DNA
<213> ORGANISM: Artificial Sequence
<220> FEATURE:
<223> OTHER INFORMATION: Synthetic sequence

<400> SEQUENCE: 150
tttcacgctg aacttcacat cggtataatc atc                                         33

<210> SEQ ID NO 151
<211> LENGTH: 24
<212> TYPE: DNA
<213> ORGANISM: Artificial Sequence
<220> FEATURE:
<223> OTHER INFORMATION: Synthetic sequence

<400> SEQUENCE: 151
ctggtgccgc gcggcagcca tatg                                                   24

<210> SEQ ID NO 152
<211> LENGTH: 23
<212> TYPE: DNA
<213> ORGANISM: Artificial Sequence
<220> FEATURE:
<223> OTHER INFORMATION: Synthetic sequence

<400> SEQUENCE: 152
ctcgaattcg gatcctcact tga                                                    23

<210> SEQ ID NO 153
<211> LENGTH: 18
<212> TYPE: DNA
<213> ORGANISM: Artificial Sequence
<220> FEATURE:
<223> OTHER INFORMATION: Synthetic sequence

<400> SEQUENCE: 153
ttgaggccgt tgagcacc                                                          18

<210> SEQ ID NO 154
<211> LENGTH: 23
<212> TYPE: DNA
<213> ORGANISM: Artificial Sequence
<220> FEATURE:
<223> OTHER INFORMATION: Synthetic sequence

<400> SEQUENCE: 154
ccggatatag ttcctccttt cag                                                    23

<210> SEQ ID NO 155
<211> LENGTH: 26
<212> TYPE: DNA
<213> ORGANISM: Artificial Sequence
<220> FEATURE:
<223> OTHER INFORMATION: Synthetic sequence

<400> SEQUENCE: 155
aatgtatagc tgcgactttg aaacca                                                 26

-continued

```
<210> SEQ ID NO 156
<211> LENGTH: 20
<212> TYPE: DNA
<213> ORGANISM: Artificial Sequence
<220> FEATURE:
<223> OTHER INFORMATION: Synthetic sequence

<400> SEQUENCE: 156
tagaggcccc aaggggttat                                              20

<210> SEQ ID NO 157
<211> LENGTH: 20
<212> TYPE: DNA
<213> ORGANISM: Artificial Sequence
<220> FEATURE:
<223> OTHER INFORMATION: Synthetic sequence

<400> SEQUENCE: 157
ataacccctt ggggcctcta                                              20

<210> SEQ ID NO 158
<211> LENGTH: 25
<212> TYPE: DNA
<213> ORGANISM: Artificial Sequence
<220> FEATURE:
<223> OTHER INFORMATION: Synthetic sequence

<400> SEQUENCE: 158
tggtttcaaa gtcgcagcta tacat                                        25
```